US011342053B2

(12) United States Patent
Tevis et al.

(10) Patent No.: US 11,342,053 B2
(45) Date of Patent: *May 24, 2022

(54) SYSTEMS AND METHODS FOR MEDICAL REFERRALS VIA SECURE EMAIL AND PARSING OF CCDS

(71) Applicant: The Advisory Board Company, Washington, DC (US)

(72) Inventors: Russell Tevis, Tucson, AZ (US); Marilyn Mamakai Agbeko, Austin, TX (US); Louis Allen Parisi, Austin, TX (US)

(73) Assignee: The Advisory Board Company, Washington, DC (US)

( * ) Notice: Subject to any disclaimer, the term of this patent is extended or adjusted under 35 U.S.C. 154(b) by 64 days.

This patent is subject to a terminal disclaimer.

(21) Appl. No.: 16/911,484

(22) Filed: Jun. 25, 2020

(65) Prior Publication Data
US 2020/0327967 A1 Oct. 15, 2020

Related U.S. Application Data

(63) Continuation of application No. 15/387,354, filed on Dec. 21, 2016, now Pat. No. 10,706,959.

(Continued)

(51) Int. Cl.
*G16H 10/60* (2018.01)
*G06F 21/62* (2013.01)
(Continued)

(52) U.S. Cl.
CPC ........... *G16H 10/60* (2018.01); *G06F 16/137* (2019.01); *G06F 16/93* (2019.01); *G06F 21/6245* (2013.01)

(58) Field of Classification Search
CPC ....... G16H 10/60; G06F 16/93; G06F 16/137; G06F 21/6245
(Continued)

(56) References Cited

U.S. PATENT DOCUMENTS

2005/0015599 A1* 1/2005 Wang .................... H04L 63/145
713/176
2006/0106644 A1* 5/2006 Koo ....................... G16H 10/60
715/224

(Continued)

OTHER PUBLICATIONS

Ferranti et al., The Clinical Document Architecture and the Continuity of Care Record: A Critical Analysis, Journal of the American Medical Informatics Association vol. 13 No. 3 May / Jun. 2006. (Year: 2006).*

(Continued)

*Primary Examiner* — Joshua B Blanchette
(74) *Attorney, Agent, or Firm* — Alston & Bird LLP

(57) ABSTRACT

Disclosed herein are various embodiments of computer-implemented methods and systems for parsing information from messages containing a standardized electronic document format, such as a continuity of care document ("CCD"), and for generating referrals and other documents using data parsed from the messages and/or standardized electronic document format. In some embodiments, a message containing a CCD may be received, the CCD and the message may be parsed to extract information (e.g., patient information), the patient information may be mapped into a document template, and an electronic document containing mapped referral parameters may be generated.

12 Claims, 14 Drawing Sheets

Related U.S. Application Data

(60) Provisional application No. 62/271,083, filed on Dec. 22, 2015.

(51) Int. Cl.
*G06F 16/93* (2019.01)
*G06F 16/13* (2019.01)

(58) Field of Classification Search
USPC .......................................................... 705/2, 3
See application file for complete search history.

(56) References Cited

U.S. PATENT DOCUMENTS

| | | | |
|---|---|---|---|
| 2007/0083403 A1 | 4/2007 | Baldwin et al. | |
| 2008/0052110 A1 | 2/2008 | Ruggirello et al. | |
| 2009/0043767 A1 | 2/2009 | Joshi et al. | |
| 2009/0112627 A1* | 4/2009 | Berkman | G16H 10/65 705/51 |
| 2011/0246231 A1* | 10/2011 | Sie | G06Q 10/10 705/3 |
| 2015/0112723 A1* | 4/2015 | Holt | G16H 10/60 705/3 |

OTHER PUBLICATIONS

U.S. Appl. No. 15/387,354, filed Dec. 21, 2016, U.S. Pat. No. 10,706,959, Issued.
U.S. Appl. No. 62/271,083, filed Dec. 22, 2015, Expired.

* cited by examiner ccd snippet

```
<patientRole>
<!--.... section removed .... -->
<providerOrganization>
<id root="2.16.840.1.113883.3.1530"/>
<name>MHMG Primary Care TMC Fannin</name>   <!--practice in CMR with two locations-->
<telecom use="WP" value="tel:(713)791-9844"/>
<addr use="WP">
<streetAddressline>7400 Fannin St., Suite 1160</streetAddressline>   <!--this is one location of the practice-->
<city>Houston</city>
<state>TX</state>
<postalCode>77054-1935</postalCode>
<country>US</country>
</addr>
</providerOrganization>
</patientRole>
```

SYSTEMS AND METHODS FOR MEDICAL REFERRALS VIA SECURE EMAIL AND PARSING OF CCDS

CROSS-REFERENCE TO RELATED APPLICATIONS

This application is a continuation of U.S. Non-Provisional Ser. No. 15/387,354, filed Dec. 21, 2016, which claims the benefit of priority from U.S. Provisional Application No. 62/271,083, filed Dec. 22, 2015, both of which are incorporated by reference herein in its entirety.

FIELD OF THE DISCLOSURE

The present disclosure relates to systems and methods for electronically parsing patient information from continuity of care documents ("CCDs") and generating electronic files, such as referrals, using the parsed patient information.

BACKGROUND

When a patient visits a doctor or, more broadly, a healthcare provider, the healthcare provider (also referred to herein as a "practice") may create or alter its clinical and/or administrative records for that patient. Practices may use electronic health records or electronic medical records systems (referred to as "EHRs" or "EMRs," respectively) in order to manage their patients' medical records. EHRs and EMRs may maintain key administrative and/or clinical data relevant to a practice's care of a patient over time, including demographic information, progress notes, medical problems, diagnostics, prescriptions, history of medical procedures, etc. Different EHRs and EMRs may have differing, and sometimes proprietary, software and architecture. In order to foster reliable interoperability of EHR and EMR systems among practices and other entities desiring access to healthcare records (e.g., general practitioners, specialists, inpatient care facilities, medical referral service providers, insurance providers, etc.), national and international standards for the transfer and exchange of clinical and administrative healthcare data have been developed. For example, Health Level 7 ("HL7") standards are a set of international standards for transferring clinical and administrative data between different software applications and platforms, such as different EHRs and EMRs.

Also among the national and international standards for the transfer of healthcare-related data are a variety of standardized data architecture and document structures for organizing, storing, and conveying heath and medical records. For example, CCDs have an XML-based document format that carry a standard structure and encoding of a patient record summary. A CCD may contain a standard organization of clinical, demographic, and administrative information for a specific patient.

Various services exist to help healthcare practices perform their administrative duties. For example, electronic referrals services are services that may allow users, such as practitioners, to request automatically generated medical referrals, based on information recorded and maintained by the practitioners' EHRs and/or EMRs. Such referrals services may rely on standards for transferring medical information, such as HL7, in order to obtain the information needed from EHRs and EMRs to generate referrals. However, even with standards such as HL7 in place, referrals services must integrate with each EHR and EMR from which a referral is requested by, e.g., establishing a dedicated connection between the referrals service and each EHR and EMR, in order to communicate with, and retrieve data from, each EHR and EMR. Integration with EHRs and EMRs is often difficult due to the cost in time, finances, and human resources. If an EHR or EMR is small, then the financial resources or technical skill required to integrate the EHR or EMR with a referrals service may simply not be available. Additionally, some EHRs and EMRs will allow integration with a referrals service, but will not grant adequate access permissions to referrals services, which may result in incomplete or unsuccessful attempts by a referrals service to retrieve data needed to generate a referral.

Practices without a referrals service integrated into an EHR or EMR, or with an EHR or EMR that grants limited permissions to a referrals service, may have to resort to manually-created (e.g., manually written or typed) referrals. Additionally, referrals services may have to either pay the time or the money to integrate their systems with non-integrated EHRs and EMRs, or else forego their capability to assist practices having non-integrated EHRs or EMRs. There therefore exists a need for systems and methods that can reliably and automatically create and/or export referrals and other medical documents in a manner consistent with standardized systems, without requiring a referrals service (or other service needing medical records) to integrate its EHR or EMR into a standard system.

SUMMARY

The present disclosure involves meeting various unmet needs in the art by disclosing methods and systems for creating electronic referral documents. In some embodiments, a computer-implemented method for creating an electronic referral document includes: receiving, at at least one computer, an electronic file having first information of a patient, wherein the first information is in a standardized format, and wherein the electronic file is sent via a secure electronic message complying with patient privacy regulations; parsing, using the at least one computer, the first information to extract second information of the patient; mapping, using the at least one computer, the second information into a template for an electronic referral document for the patient; and generating the electronic referral document containing the mapped second information.

In some embodiments, the electronic file is a continuity of care document (CCD) for the patient. In further embodiments, the electronic referral document contains a referral for one of acute care, ambulatory care, post-acute care, imaging procedures, laboratory procedures, or other diagnostic or therapeutic procedure. In yet further embodiments, the standardized format is a standardized extensible markup language (XML) architecture. In yet further embodiments, the electronic file is received from a first healthcare entity having an electronic medical records (EMR) or electronic health records (EHR) system, and the parsing, mapping, and generating steps are performed by at least one second entity, wherein the at least one second entity is not integrated into the EMR or EHR system of the first healthcare entity.

In further embodiments, the second entity sends the electronic referral document to at least one of a healthcare practice, a specialist, a patient, or an insurance provider. In still further embodiments, receiving the electronic file includes receiving the secure electronic message from a healthcare practice; and the method further includes extracting the electronic file from the secure electronic message, and determining whether an authorization exists for at least one of the parsing, mapping, and generating steps. In further embodiments, the method further includes if the authorization does not exist, determining if the extracted electronic file corresponds to a previously-generated electronic referral document.

In yet further embodiments, the electronic file is a CCD, the secure electronic message is a Direct message, and the method further includes extracting the CCD from the secure electronic message, and attaching the CCD to the generated referral document to make a referral package. In further embodiments, the secure electronic message includes the CCD as a first attachment, the secure electronic message further includes a second attachment, and the method further includes extracting the CCD and the second attachment from the secure electronic message, attaching the CCD and the second attachment to the generated electronic document to make an electronic package, and sending the electronic package to at least one of a healthcare practice, a specialist, a patient, or an insurance provider.

In some embodiments, a computer-implemented method for creating an electronic referral document includes: receiving, at at least one computer, an electronic CCD having first information of a patient, wherein the first information is in a standardized format, and the CCD is received from a first healthcare entity having an EMR or EHR system; and creating an electronic referral document by at least one second entity, wherein the at least one second entity is not integrated into the EMR or EHR system of the first healthcare entity, and wherein creating the electronic referral document includes the steps of: parsing, using the at least one computer, the first information to extract second information of the patient; mapping, using the at least one computer, the second information into a template for an electronic referral document for the patient; and generating the electronic referral document containing the mapped second information.

In further embodiments, the method further includes attaching the CCD to the generated electronic referral document to create a referral package, and sending the referral package to at least one of a healthcare practice, a specialist, a patient, or an insurance provider. In some embodiments, the step of receiving the CCD includes receiving a secure message complying with patient privacy regulations and containing the CCD, and the step of creating an electronic referral document by at least one second entity further includes extracting the CCD from the secure message. In some embodiments, the method further includes attaching the CCD to the generated electronic referral document to create a referral package, and storing the referral package in a database.

In further embodiments, the step of creating the electronic referral document further includes determining whether the at least one second entity has received an authorization from the first healthcare entity to perform one or more of the parsing, mapping, or generating steps, and if the second entity has not received the authorization, then (1) determining whether the CCD corresponds to a previously-generated electronic referral document and (2) if the CCD corresponds to a previously-generated electronic referral document, attaching the CCD to the previously-generated electronic referral document to create a referral package.

In further embodiments, the step of creating the electronic referral document further includes determining whether the received CCD is a duplicate of a previously-received CCD by creating a hash using the received CCD, storing the created hash in a database, and comparing the created hash to previously generated and stored CCD hashes in the database.

In some embodiments, a system for creating an electronic referral document includes at least one computer comprising computer executable instructions, the instructions causing the at least one computer to: receive an electronic file having first information of a patient, wherein the first information is in a standardized format, and wherein the electronic file is sent via a secure electronic message complying with patient privacy regulations; parse the first information to extract second information of the patient; map the second information into a template for an electronic referral document for the patient; and generate the electronic referral document containing the mapped second information.

In further embodiments, the electronic file is a CCD, and the standardized format is an XML, architecture, and the instructions further cause the at least one computer to determine whether the CCD is a duplicate of a previously-received CCD by extracting the CCD from the secure electronic message, creating a hash using the CCD, and comparing the created hash to a database of previously-created hashes.

In further embodiments, the secure electronic message is sent from a first healthcare entity, the at least one computer is located at a second entity, and the instructions further cause the at least one computer to determine whether the first healthcare entity has authorized the second entity to generate the electronic referral document, if the first healthcare entity has not authorized the second entity to generate the electronic referral document, determine whether the CCD corresponds to a previously-generated referral document, and if the CCD corresponds to a previously-generated referral document, attach the CCD to the previously-generated referral document.

In further embodiments, the CCD is received as a first attachment to the secure electronic message from the first healthcare entity, the secure message further including a second attachment, and the instructions further cause the at least one computer to extract the CCD and the second attachment from the secure electronic message, attach both the CCD and the second attachment to the generated electronic referral document to create an electronic referral package, and send the electronic referral package to at least one of a healthcare practice or an insurance provider.

Any of the embodiments illustrated above and below stand independently or features may be combined to achieve preferred embodiments. Additional advantages and embodiments of the disclosure will also become more apparent to those of ordinary skill in the art upon review of the teachings of the present application.

BRIEF DESCRIPTION OF DRAWINGS

Further advantageous features of the present disclosure will become more apparent with the following detailed description when taken with reference to the accompanying drawings, in which:

FIG. 3 illustrates an exemplary snippet of a continuity of care document ("CCD"), in accordance with one or more embodiments of the present disclosure;

FIG. 14 depicts a screenshot from an exemplary graphical user interface associated with a software implementation of an embodiment of the present disclosure.

Figure 1:
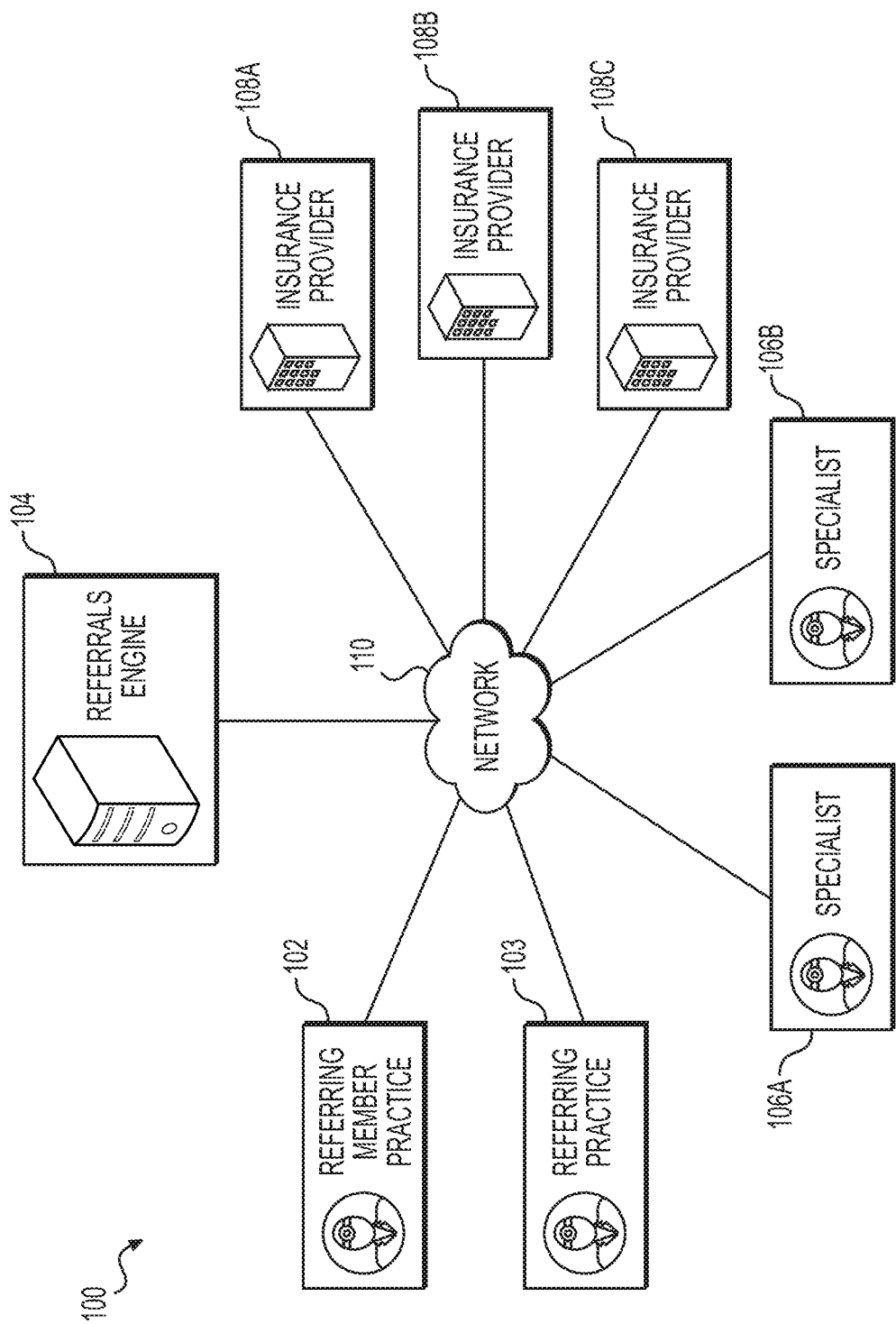
FIG. 1 illustrates an exemplary system, wherein referring practices, specialists, insurance providers and a referrals platform are functionally interconnected through an electronic network, in accordance with one or more embodiments of the present disclosure.

The systems and diagrams in the Figures illustrate the architecture, functionality and operation of possible implementations of systems, methods and computer program products, according to various embodiments of the present disclosure. In this regard, each block or icon in the diagrams may represent a module, segment, or portion of code, which comprises one or more executable instructions for implementing the specified logical function(s). The diagrams and other figures depicted herein are just examples. There may be many variations to each diagram or the steps (or operations) described therein without departing from the spirit of the disclosure. It should also be noted that, in some alternative implementations, the functions noted in each block may occur out of the order noted in the figures. For example, two blocks shown in succession may, in fact, be executed substantially concurrently, or the blocks may sometimes be executed in the reverse order, depending upon the functionality involved. It will also be noted that each block or icon of the system and workflow diagrams and/or flowchart illustration, and combinations of blocks and/or icons in the system and workflow diagrams and/or flowchart illustration, may be implemented by special purpose hardware-based systems that perform the specified functions or acts, or combinations of special purpose hardware and computer instructions.

DETAILED DESCRIPTION OF THE EMBODIMENTS

Standardized electronic document formats, such as CCDs, may be a tool with which a practice can convey patient summary data to, e.g., a referrals service or other medical records service, without requiring the referrals service or other medical records service to be integrated into the practice's EHR or EMR. The referrals service or other medical records service may parse patient information from a received file in a standardized electronic document format, and may generate a referral or other healthcare-related document using the parsed patient information.

Disclosed herein are various embodiments of computer-implemented methods and systems for parsing information from messages containing a standardized electronic document format, such as a CCD, and for generating referrals and other documents using data parsed from the messages and/or standardized electronic document format. The referrals service or other medical records service may receive the messages directly from a health care practice, although having the message proceed indirectly to the service (e.g., through an intermediary) is also contemplated in embodiments herein. For the sake of simplicity, the present disclosure will describe the embodiments herein by referring to "CCDs" and to generating "referrals"; however, it should be understood that standardized electronic document formats other than CCDs may also be contemplated for use in the present disclosure, and that electronic documents other than referrals may be generated according to the systems and/or methods disclosed herein. It will be apparent to those of ordinary skill in the art that alternative embodiments of the implementations described herein may be employed and still fall within the scope of the claimed invention. It will be understood that the invention is not limited to the specific embodiments disclosed herein but may be capable of numerous modifications by one of ordinary skill in the art. It will be further understood that the devices used and technological details may be slightly different or modified from the descriptions herein without departing from the methods and systems disclosed and taught by the present invention. Other variations and modifications will be apparent to those of ordinary skill in the art.

For the purposes of this document, a "practice" or "practices" (also referred to herein as "practitioners") may broadly include clinicians, medical specialists, hospitals, hospital groups, care settings, insurers, employers providing health care benefits, health care service industries, and other individuals, organizations and groups related to health-care delivery or administration.

The present disclosure may allow practices to request a referral or other document by sending a message including, e.g., a CCD, directly to a referrals service or other medical records service. For example, practices may wish to create a patient referral to be forwarded to an insurance provider or a medical specialist. As another example, an inpatient facility, such as a hospital or long-term care facility, may wish to create a transfer of care document, in order to transfer acute (inpatient) care of a patient from one division within the facility to another, or from one facility to another facility. Practices need not have an EHR or EMR system integrated with a referrals system, in order to send (e.g., directly) a message including CCD architecture to the referrals system and have a referral be automatically created, updated, and/or forwarded to an insurance provider or another practice. Thus, advantageously, practices may order automatically-generated, reliably-created referrals according to systems and methods disclosed herein, without having to incur the expense and time of integrating their EHR or EMR systems with a referrals service or other service. According to some embodiments disclosed herein, practices having an EHR or EMR that is integrated with a referrals service may also request a referral or other document by sending a message including a CCD to the referrals service.

Reference will now be made to the figures accompanying the specification.

FIG. 1 illustrates a network system 100 in which exemplary embodiments of the present disclosure may operate. The network system 100 may include any type of interconnected computer technologies and/or devices (including mobile devices (e.g., smartphones and/or tablets), computers and other hardware, including specialized machines and computers specifically programmed to execute precise instructions, having a processor and a repository for data or connection to a repository for maintained data) (interchangeably referred to herein as "computers"). Network system 100 may be public or private, or a hybrid thereof. Network system 100 may include, for example, network backbones, long-haul telephone lines, internet service providers, routers, switches, wireless connections, and/or other means for routing data/information between computers.

Network system 100 may include various individuals, organizations, clients, and/or systems connected to network system 100 via computers. For example, network system 100 may include an integrated referring practice 102, a referring practice 103, a referrals platform 104, specialist systems 106a, 106b, and/or insurance provider systems 108a, 108b, 108c, which all may be directly coupled to a network 110. Each of the integrated referring practice 102, referring practice 103, referrals platform 104, specialist systems 106a, 106b, and/or insurance provider systems 108a, 108b, 108c may include one or more computers with which to communicate data/information through network 110 and/or directly with one another using any desired network connection. In some embodiments and implementations of network system 100, the one or more computers may include one or more terminals (also referred to herein as "devices") allowing for input and review of information by individuals providing health-related services to patients, such as one or more graphical displays, speakers, keyboards, mice, touchpads, voice-recognition devices, microcomputers, personal computers, portable personal computers (e.g., notebook, laptop, netbook, minicomputer), server computer systems, ultraportable device (e.g., telephones or smartphone devices, personal digital assistants (PDAs), tablets), consoles, or other devices having a processor and input capability, and the like.

Network 110, as well as network connections made directly between two or more computers in network system 100, may include any network or direct connections that would be understood to one skilled in the art. For example, network 110 and/or direct connections in network system 100 may include wired, wireless, and/or fiber optic connections. Network 110 and/or direct connections in network system 100 may include, for example, a local area network (LAN), wide area network (WAN), personal area network (PAN), near me area network (NAN), home area network (HAN), storage area network (SAN), campus area network (CAN), metropolitan area network (MAN), backbone network, enterprise private network, virtual private network (VPN), or any combination thereof. Network 110 and/or direct connections in network system 100 may also include near field communication (NFC) and/or Bluetooth network standards. In some embodiments, network 110 and/or direct connections in network system 100 may include the Internet. For example, network 110 may be the Internet.

Integrated referring practice 102 may be a practice having an EHR or EMR that is integrated with, e.g., a referrals service, via a standard system for transferring healthcare information (e.g., HL7). Integrated referring practice 102 may be, for example, any practice, such as a physician, physician's office, clinic, nurse, nursing practice, dentist, pharmacist, medical or pharmacy technician, surgeon, therapist, pathologist, medical laboratory, medical laboratory scientist, midwife, emergency medical personnel, hospital, etc., or a network of such practices. Integrated referring practice 102 may also be referred to as a "member" of a referral service that is integrated with its EHR or EMR.

Integration with, e.g., a referrals service may include, for example, establishment of a dedicated connection between the referrals service and integrated referring practice 102. A dedicated connection may include one or more of, e.g., implementation of one or more dedicated networks to create a link between a referrals service and integrated referring practice 102 (e.g., a virtual private network ("VPN")), adaptation of an EMR or EHR of referring practice 102 to communicate with a dedicated network, implementation of one or more servers reserved for integration by one or more of, e.g., integrated referring practice 102 and/or referrals platform 104, implementation and/or upkeep of a dedicated user interface for the referrals service for use by, e.g., integrated referring practice 102, implementation of one or more electronic storage systems dedicated for a referrals service, retention of a dedicated advisor (e.g., one or more individuals) to guide implementation and drive adoption of, e.g., referrals service technology, implementation of monitoring systems and/or testing procedures to ensure proper functioning of the referrals service and/or the dedicated connection, and/or other dedication of human and/or technological resources by the referrals service and/or integrated referring practice 102.

Referring practice 103 may be, for example, a practice having an EHR or EMR system that is not integrated with a referrals service. Referring practice 103 may also be, for example, any practice, such as any of the types of individuals and organizations that may be an integrated referring practice 102.

Referrals platform 104 may be, for example, a computer or multiple computers connected together, such as a server or a series of servers, that is configured to receive and send data/information to and from integrated referring practice 102, referring practice 103, specialists 106a, 106b, insurance providers 108a, 108b, 108c, and/or other computers, systems, individuals, and/or organizations that may be connected to network system 100. Referrals platform 104 may be configured to receive, store, parse, create, organize, and/or modify healthcare-related information, documents, and data, such as CCDs, patient test results, referrals, referral requests, insurance claims, insurance records, etc. Referrals platform 104 may be configured to, e.g., provide a referrals service or other document creation service to integrated referring practice 102 and/or referring practice 103. In some embodiments, a referrals service provided by referrals platform 104 may be integrated with an EHR or EMR of integrated referring practice 102 via a standard for transferring healthcare information, such as HL7. Referrals platform 104 may also be configured to receive and parse electronic messages containing attached CCDs and/or other documents, sent to and from integrated referring practice 102, referring practice 103, specialists 106a, 106b, insurance providers 108a, 108b, 108c, and/or other computers, systems, individuals, and/or organizations that may be connected to network 110. Referrals platform 104 may further be configured to create or modify electronic documents, such as referrals, using the received and parsed electronic messages and attachments.

Specialists 106a, 106b may be, for example, practices to which integrated referring practice 102 and referring practice 103 may refer patients for medical care. Specialists 106a, 106b may each be, for example, any individual or organization that provides health-related services to patients and to whom patients may be referred, such as any of the types of individuals and organizations that may be an integrated referring practice 102.

Insurance providers 108a, 108b, 108c may be, for example, systems or organizations that provide health insurance benefits to patients. Insurance providers 108a, 108b, 108c may be public or private providers of health insurance. In some embodiments, insurance providers may be able to receive electronic documents, such as referrals and insurance claims, from one or more of integrated referring practice 102, referring practice 103, referrals platform 104, and/or specialists 106a, 106b.

One of ordinary skill in the art will understand that while network system 100 depicts an exemplary system having one integrated referring practice 102, one referring practice 103, two specialists 106a, 106b, three insurance providers 108a, 108b, 108c, and one referrals platform 104, network system 100 may include any number of each of these participants in network system 100.

Figure 2:
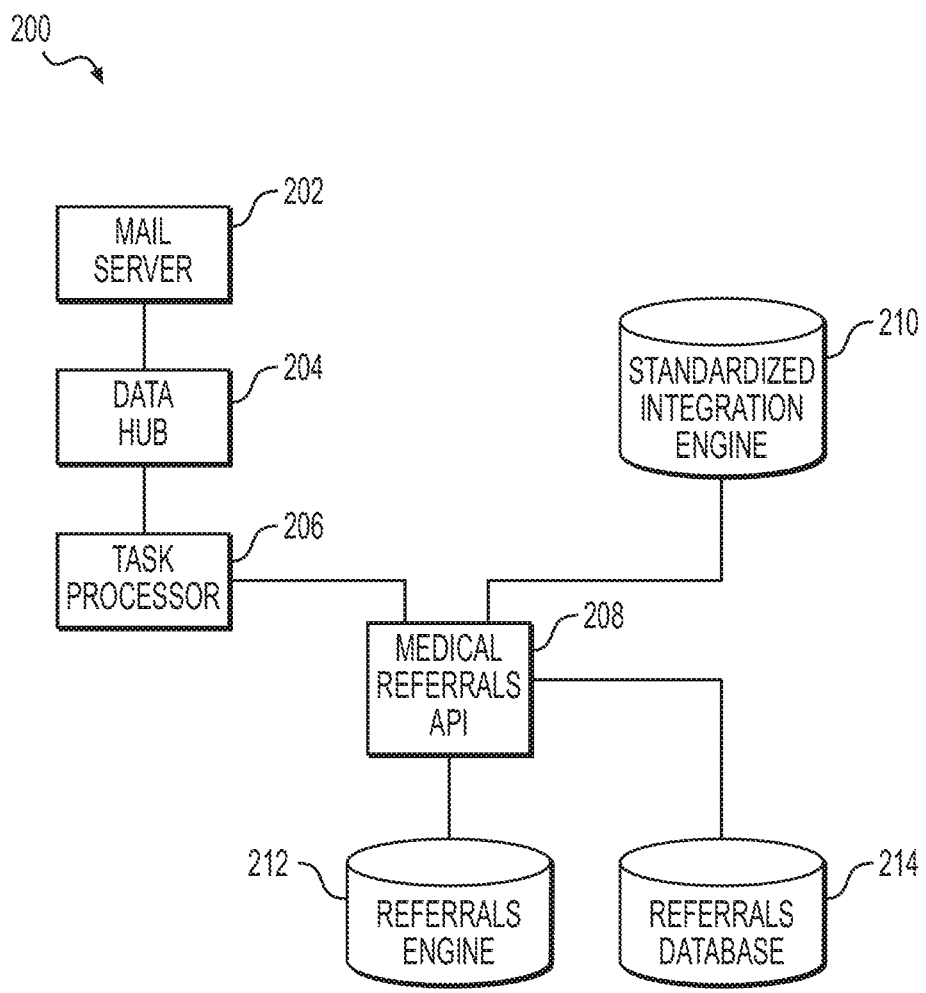
FIG. 2 illustrates an exemplary system, in accordance with one or more embodiments of the present disclosure.

FIG. 2 illustrates an exemplary system diagram that may exist over network system 100, in accordance with some embodiments described herein. FIG. 2 depicts a referrals system 200 including a mail server 202, a data hub 204, a task processor 206, a medical referrals application program interface ("API") 208, a standards-integrated engine 210, a referrals engine 212, and a referrals database 214. Mail server 202 may be connected, for example, to data hub 204. Data hub 204 may be connected, for example, to task processor 206. Task processor 206 may be connected to medical referrals API 208. Medical referrals API 208 may also be connected to standards-integrated engine 210, referrals engine 212, and referrals database 214.

The connections between mail server 202, data hub 204, task processor 206, medical referrals API 208, standards-integrated engine 210, referrals engine 212, and/or referrals database 214 may be any connection known to those of ordinary skill in the art. In some embodiments, one or more of the connections between mail server 202, data hub 204, task processor 206, medical referrals API 208, standards-integrated engine 210, referrals engine 212, and/or referrals database 214 may be, for example, a network connection, such as any of the connections described with respect to network system 100. In some embodiments, one or more of these connections may be, for example, a direct connection, such as direct connections that have been previously described herein. In further embodiments, one or more of mail server 202, data hub, 204, task processor 206, medical referrals API 208, standards-integrated engine 210, referrals engine 212, and/or referrals database 214 may be located on or within the same physical structure. For example, in some embodiments, data hub 204 and task processor 206 may be both located on a single computer. As another example, medical referrals API 208, referrals engine 212, and referrals database 214 may all be located on a single computer.

Mail server 202 may be, for example, a server configured to receive and route electronic messages from and to individuals, organizations, or computers, e.g., over network system 100. In some embodiments, mail server 202 may be an email server, such as a simple mail transfer protocol (SMTP) server. In some embodiments, mail server 202 may be a secure short message server. In some cases, mail server 202 may be required to meet certain government regulations and/or standard protocols, such as those relating to patient privacy (e.g., HIPAA standards), and to security. In further embodiments, mail server 202 may be a mail server meeting a national and/or international security standard, such as a Direct standard (e.g., Direct Project, Direct Exchange, and/or Direct Secure Messaging), configured to receive and route messages from and to individuals, organizations, or computers according to the security standard. In some embodiments, mail server 202 may be one or more health internet exchanges ("HIEs") managing a network of authorized message senders and/or recipients according to established national and/or international security standards. Individuals and organizations, such as integrated referring practice 102, referring practice 103, specialists 106a, 106b, and/or insurance providers 108a, 108b, 108c may have electronic messaging accounts capable of transferring messages via mail server 202. For example, if mail server 202 is an HIE configured to route Direct messages, then integrated referring practice 102, referring practice 103, specialists 106a, 106b, and/or insurance providers 108a, 108b, 108c may have Direct message accounts. Mail server 202 may be connected to data hub 204 via, for example, a network, such as network 110. In some embodiments, integrated referring practice 102, referring practice 103, specialists 106a, 106b, and/or insurance providers 108a, 108b, 108c may have electronic message accounts associated with multiple different mail servers, any and/or all of which may be connected to data hub 204.

Data hub 204 may be, for example, a computer or computers housing executable instructions to receive various data and/or information from, e.g., mail server 202, organize the received data and/or information based on characteristics of the data and/or information, and forward the data in organized form to a task processor 206. In some embodiments, data hub 204 may be particularly configured to receive electronic messages containing CCDs and other documents from integrated referring practice 102 and/or referring practice 103 via mail server 202, and to sort the received electronic messages into task queues based on the contents of each message. In some embodiments, for example, data hub 204 may be configured to sort electronic messages into one queue for messages containing CCDs for patients undergoing acute care (e.g., inpatient care) and another queue for messages containing CCDs for patients in ambulatory (e.g., outpatient) care, based on, e.g., an indication in each electronic message and/or CCD that the patient whose health information is in the electronic message and/or CCD is undergoing acute care or ambulatory care. For example, an electronic message and/or CCD may contain an element or instruction to create a referral for a patient undergoing acute care (such as, for example, a transfer of care document), or an instruction to create a referral for a patient undergoing ambulatory care (such as, for example, an outpatient referral). In further embodiments, data hub 204 may be configured to sort electronic messages into queues for messages containing CCDs for patients undergoing, or potentially undergoing, post-acute care, imaging procedures at, e.g., an imaging facility, laboratory procedures at, e.g., a laboratory, and other diagnostic or therapeutic procedure, and/or other types of patient care.

Task processor 206 may be, for example, a computer or computers housing executable instructions to receive queues of messages from, e.g., data hub 204, parse each message to determine and identify its contents, and to forward parsed messages and their contents (including, e.g., CCDs) to medical referrals API 208.

Medical referrals API 208 may be, for example, a series of electronic protocols housed on a computer or computers. The series of protocols may allow medical referrals API 208 to receive parsed messages and their contents, determine whether a referral needs to be created, issue directions to referrals engine 212 if a referral needs to be created, attach documents to newly-created and/or existing referrals, and store messages, their attachments, referrals, and records of the referral creation process in referrals database 214. Medical referrals API 208 may also be configured to receive, store, and modify referrals from standards-integrated engine 210.

Standards-integrated engine 210 may be, for example, a computer or series of computers housing software that may be integrated with an EHR or EMR of integrated referring practice 102. Standards-integrated engine 210 may be integrated with an EHR or EMR of integrated referring practice 102 by, e.g., establishment of a dedicated connection between standards-integrated engine 210 and integrated referring practice 102, as has previously been described herein. Standards-integrated engine 210 may be configured to receive, for example, an order to create a referral or other healthcare-related document from integrated referring practice 102. Standards-integrated engine 210 may also include data storage (e.g., hard drive or cloud storage) and/or one or more databases for storing and recording created referrals. Standards-integrated engine 210 may also be configured to forward referrals, e.g., referrals that it has created, to medical referrals API 208.

Referrals engine 212 may be, for example, a computer or series of computers housing executable instructions which allow it to generate referrals from messages containing CCDs. Referrals engine 212 may be configured to receive messages, CCDs, and instructions to generate referrals using the received messages and CCDs from, e.g., medical referrals API 208. Referrals engine 212 may further be configured to return created referrals to medical referrals API 208. Referrals engine 212 may also include a database or databases of data structures which may provide referrals engine 212 with a structure into which it may extract data from a CCD or other standardized document format, organize the data, and accurately populate a referral or other document with the organized data.

Referrals database 214 may be, for example, a computer or series of computers housing electronic storage in which medical referrals API 208 may store data relating to referral requests and creation, such as referral requests, created referrals, documents to be attached to referrals, referral statuses, etc. Referrals database 214 may be accessible by medical referrals API 208. In some embodiments, referrals database 214 may also be accessible by referrals engine 212 and standards-integrated engine 210.

In some embodiments, data hub 204, task processor 206, medical referrals API 208, standards-integrated engine 210, referrals engine 212, and referrals database 214 may all be integrated within a single computer or group of computers included in referrals platform 104. In other embodiments, one or more of data hub 204, task processor 206, medical referrals API 208, standards-integrated engine 210, referrals engine 212, and referrals database 214 may be independent computers or systems in one or more geographic locations, connected via one or more network or direct connections.

As can be seen in, e.g., FIG. 2, medical referrals API 208 may receive data from both mail server 202 and standards-integrated engine 210. Thus, in some embodiments disclosed herein, medical referrals API 208 and referrals engine 212 may advantageously receive sufficient information to, e.g., create referrals from messages containing CCDs, that were received via mail server 202 from a (non-standards-integrated) referring practice 103, despite referring practice 103 not being integrated with a referrals service.

One of ordinary skill in the art will understand that while referrals system 200 depicts an exemplary system having one mail server 202, one data hub 204, one task processor 206, one medical referrals API 208, one standards-integrated engine 210, one referrals engine 212, and one referrals database 214, referrals system 200 may include any number of each of these participants in referrals system 200.

FIG. 3 depicts a snippet, or portion, of an exemplary CCD 300. As previously stated, while this disclosure refers to CCDs in particular, CCDs are an example of a standardized document structure, and the modification of the present disclosure to use other standardized document structures may be within the purview of one of ordinary skill in the art. CCD 300 may be an electronic file, such as an electronic document, containing information about or related to a patient. As is further described elsewhere, CCD 300 may be an electronic file, such as an electronic document, that may be created, modified, stored, secured, transferred, organized, and/or attached with other electronic documents by authorized individuals, organizations, clients, systems, and/or engines, e.g., integrated referring practice 102, referring practice 103, referrals engine 104, specialists 106a, 106b, and/or insurance providers 108a, 108b, 108c, using one or more computer systems, such as, e.g., mail server 202, data hub 204, task processor 206, medical referrals API 208, standards-integrated engine 210, referrals engine 212, and/or referrals database 214.

In some embodiments, CCD 300 may be an electronic file written in a self-describing electronic language. For example, CCD 300 may be written in extensible markup language ("XML"). In some embodiments, CCD 300 may be organized as a standardized set of elements (e.g., XML elements) for summarizing patient information, specified by one or more standards-setting organizations, such as Health Level 7 ("HL7") and/or the American Society for Testing and Methods ("ASTM"). For example, CCD 300 may have a standardized architecture developed by HL7 and ASTM. In some embodiments, CCD 300 may have a format and scope determined by a standardized specification (e.g., the Continuity of Care Record developed by ASTM).

CCD 300 may include various elements that describe aspects of patient data. As depicted in FIG. 3, CCD 300 may include various XML elements and subelements related to categories of patient information. For example, CCD 300 may include an element for specifying a patient's identifying information as it relates to a particular healthcare practice ("<patientRole>"). CCD 300 may also include subelements to further organize information within elements and subelements, such as an element for specifying a healthcare practice relevant to the <patientRole> element ("<providerOrganization>"), which may be a subelement to the <patientRole> element. The <providerOrganization> element may include further subelements, such as a name subelement for specifying a healthcare practice's name, a telecommunications subelement for specifying a telephone or fax number at which to reach the practice, and subelements for portions of the practice's mailing address. Further elements and subelements of CCD 300 (not depicted in FIG. 3) may be directed to, e.g., a purpose of CCD 300, a table of contents for CCD 300, patient problems, medical procedures, patient family history, patient social history, payers for the patient, advance directives for the patient, alerts, medications, immunizations, medical equipment, vital signs, functional statistics, results of tests and/or medical treatments, patient counters, and/or a plan of care, etc. These and other elements and subelements related to categories of patient information, and their organization within CCD 300, may be contemplated and understood by those of ordinary skill in the art.

Figure 4:
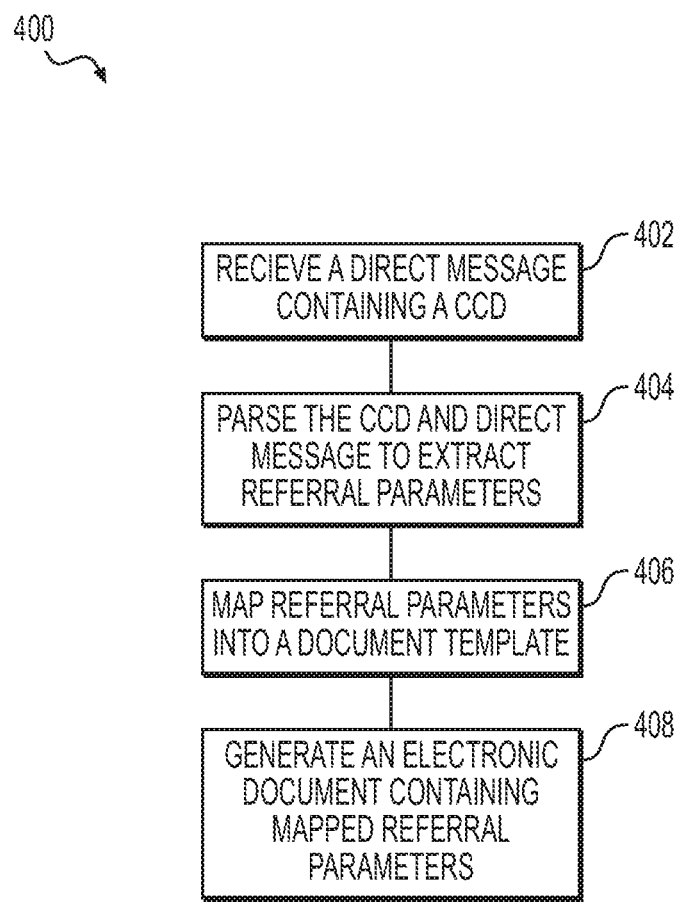
FIG. 4 illustrates an exemplary flow diagram of a process of generating an electronic document based on a received message containing a CCD, in accordance with one or more embodiments of the present disclosure.

FIG. 4 depicts a flow diagram for an exemplary method 400 according to the present disclosure. In step 402, a message containing a CCD may be received. In step 404, the CCD and the message may be parsed to extract information (e.g., patient information). In step 406, the patient information may be mapped into a document template. In step 408, an electronic document containing mapped referral parameters may be generated.

According to step 402, a message containing a CCD may be received. The message containing the CCD may be received by, for example, referrals engine 212. In some embodiments, the message containing the CCD may be received by medical referrals API 208, which may then forward the message containing the CCD to referrals engine 212. In some embodiments, the message containing the CCD may be a Direct message, and may be received by a system configured to receive Direct messages at, e.g., a secure Direct account.

In further embodiments, the message containing the CCD may first be received by data hub 204, which may sort the message based on its contents and then forward the sorted message to task processor 206, which may parse the message into a message packet and attachment or attachments. In some embodiments, the CCD may be one of a plurality of attachments to the parsed message. Task processor 206 may then forward the parsed message packet and attachments to the medical referrals API 208, which may in turn forward the message and attachments to referrals engine 212.

According to step 404, the CCD and the message may be electronically parsed to extract information. In some embodiments, this may be accomplished by electronically identifying elements within the CCD and the message, such as, for example, elements defined by XML, tags, and copying or transferring the identified elements to a data structure, such as a mapping table or database. For example, a location for a referring practice 103 or integrated referring practice 102 may be determined by, e.g., analyzing an electronic address from which the message and CCD were sent, and comparing the address to a managed database of all addresses and locations from which messages and CCDs are accepted. Once the electronic address is located in the database, the corresponding location of the referring practice 103 or integrated referring practice 102 may be determined. Alternately, a location for a referring practice 103 or integrated referring practice 102 may be looked up, e.g., in a public directory or on the Internet, based on the address from which the message and CCD were sent.

In some embodiments, identified elements within the CCD may be used to extrapolate further information. For example, a patient or provider ID number in the CCD may be compared to a database of patient or provider ID numbers in order to identify a patient or provider name, or a provider location, associated with the ID number.

In some embodiments, step 404 may be accomplished by referrals engine 212. In further embodiments, step 404 may be performed by a combination of data hub 204, task processor 206, medical referrals API 208, and/or referrals engine 212.

According to step 406, the patient information may be mapped into a document template to, for example, begin creating an electronic document such as a referral. In some embodiments, this may be accomplished by referring to a mapping table or database that has been populated by information parsed from the CCD and/or the message, and copying or transferring information from the mapping table or database to a document template. A document template may be, for example, an electronic file or document encoded in a markup language or other computer-readable language. In some embodiments, a document template may be a referral template with a standardized structure. In some embodiments, this step may be performed by, e.g., referrals engine 212. In further embodiments, step 406 may be performed by a combination of data hub 204, task processor 206, medical referrals API 208, and/or referrals engine 212.

According to step 408, an electronic document containing mapped referral parameters may be generated. In some embodiments, this may be accomplished by, for example, saving a populated instance of a document template, or executing computer-readable language in order to create and/or publish an exportable form of the document. In some embodiments, step 408 may be accomplished by, e.g., referrals engine 212. In further embodiments, step 408 may be accomplished by, e.g., referrals engine 212 and/or medical referrals API 208. In some embodiments, the created electronic document may be stored in a computer storage medium, such as a database. In other embodiments, the created electronic document may be transmitted to a designated recipient. For example, if the electronic document is a referral, it may be transmitted to, e.g., one or more of specialists 106a, 106b or one or more of insurance providers 108a, 108b, 108c. In further embodiments, the created electronic document may be transmitted to a referring practice 103 or an integrated referring practice 102 that requested creation of the document by sending the message containing the CCD that was received in step 402. In yet further embodiments, the created electronic document may be transmitted to, e.g., a patient to whom the document relates over, e.g., network 110.

In some embodiments, a message containing a CCD may not have enough information to fill a document template with patient information according to method 400. Alternately or additionally, the parsing and mapping steps may not be performed successfully on all aspects of patient information within a message or CCD. In such cases, a partially-mapped electronic document may be created. Alternately, a document template may be partially mapped and then stored for auditing or later completion, upon receipt of additional data.

Figure 5:
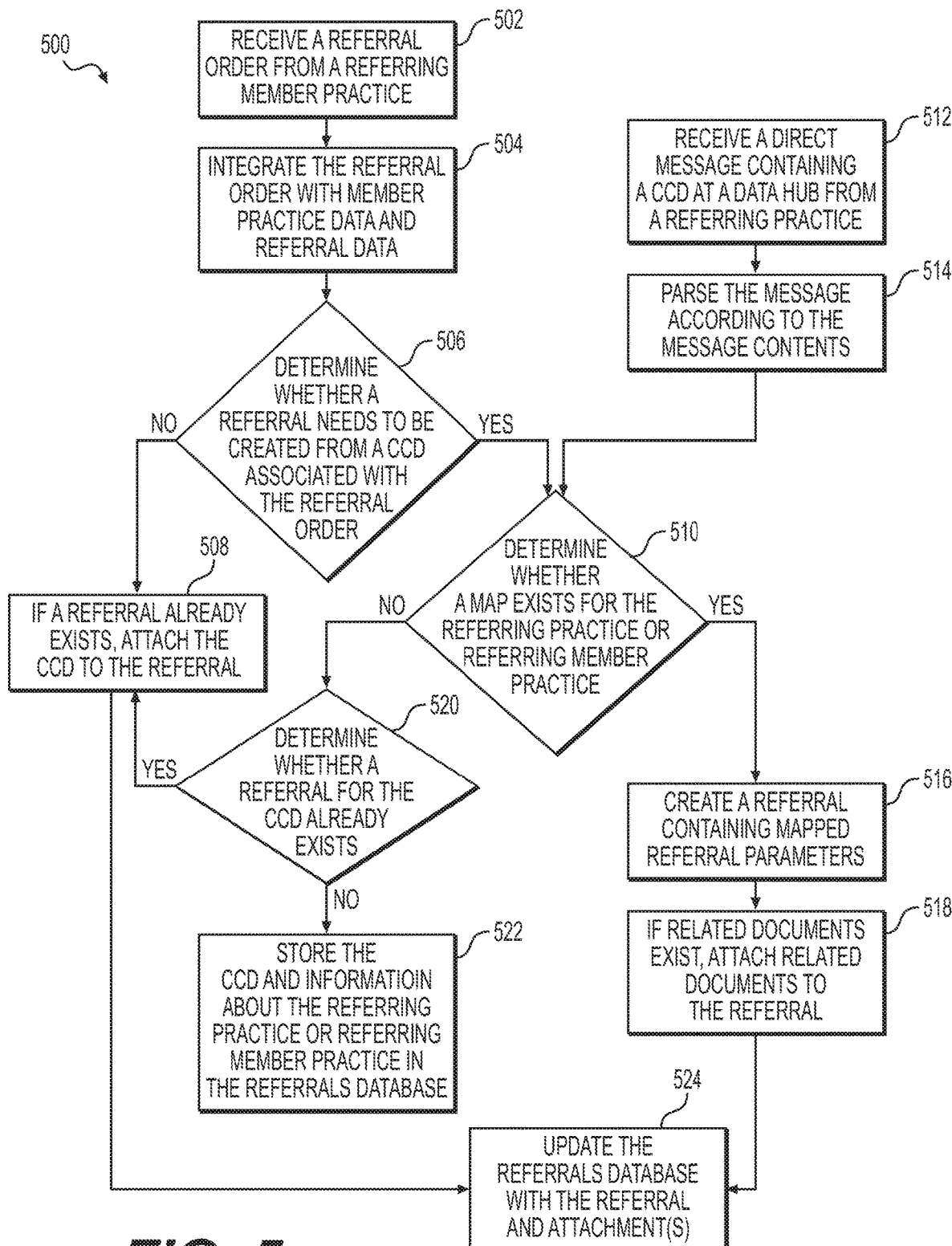
FIG. 5 illustrates a further exemplary flow diagram of a process of managing information contained in a CCD.

FIG. 5 illustrates a system flow 500 that incorporates a method of creating a referral from a CCD according to the present disclosure, into an existing method for creating a referral. For example, steps 502, 504, and 505 illustrate a known method of creating a referral using a standards-integrated engine. According to step 502, a referral order may be received from an integrated referring practice. According to step 504, a referral may be created using a standards-integrated engine. And according to step 505, the created referral may be stored. The remainder of the steps illustrated in FIG. 5 incorporate a method of creating a referral according to the present disclosure, directly from a CCD. For example, according to step 510, a message may be received containing a CCD. According to step 512, the message may be sorted and parsed according to its contents. According to step 516, the CCD may be extracted from the message. According to step 518, whether a map exists that may be associated with the CCD may be determined. If a map does not exist, then flow may continue to step 506. According to step 506, whether a CCD received via a message matches a stored referral may be determined. According to step 508, if a match exists between a stored referral and a CCD, the CCD may be attached to the created referral. According to step 509, the referral and attached CCD may then be exported and/or stored. According to step 520, if no match exists between the CCD and a stored referral, then the CCD may be stored. If a map does exist for a referring practice associated with the CCD, flow may continue to step 522. According to step 522, a referral may be created containing mapped parameters from the CCD and message. According to step 524, the CCD may be attached to the created referral. Flow may then continue to step 509, where the referral and attached CCD may be exported and/or stored.

Referring now to step 502, a referral order may be received from an integrated referring practice, such as, e.g., integrated referring practice 103. In some embodiments, the referral order may be received at standards-integrated engine 210. In some embodiments, the referral order may be made by integrated referring practice 103 via, for example, a referrals service interface. According to step 504, a referral may then be created. In some embodiments, standards-integrated engine 210 may create the referral by accessing the EHR or EMR of integrated referring practice 103 using, for example, standards for transferring healthcare information (e.g., HL7 standards). According to step 505, the created referral may be stored in, e.g., a database or storage system associated with standards-integrated engine 210. In some embodiments, the created referral may be forwarded to a medical referrals API such as medical referrals API 208, and stored in, e.g., referrals database 214.

According to step 510, in a separate branch of the flow, a message containing a CCD may be received. In some embodiments, the message containing the CCD may be received by, e.g., data hub 204, task processor 206, and/or medical referrals API 208. According to step 512, the message may be sorted and/or parsed according to its contents. In some embodiments, the CCD may be contained in the message as, e.g., an attachment. In some embodiments, the message may include multiple attachments, one of which may be the CCD. Other attachments may include, for example, medical data, notes, test results, images, laboratory results, etc. pertaining to a patient associated with the CCD. Steps 510 and 512 may be performed in similar fashion to, and by similar systems as, e.g., steps 402 and 404 of method 400, as described above.

According to step 516, the CCD may be extracted from the message by, for example task processor 206 or medical referrals API 208. This may be accomplished by, for example, digitally creating a copy of the CCD separately from the message. This step may allow for analysis of the CCD separately from the message. In some embodiments, if the message includes multiple attachments, the CCD and other attachments may be extracted from the message as a part of this step.

According to step 518, whether a map exists that is associated with the extracted CCD may be determined by, e.g., medical referrals API 208. Maps may be collections of identifying data in a database, e.g., referrals database 214, that may, for example, correspond to certain authorizations, decision trees, systems, etc. that may provide direction as to whether to continue with a referral creation process. For example, a map may be a collection of identifying data that corresponds to a CCD. As another example, a map may be a collection of identifying data that corresponds to an integrated referring practice 102 and/or a referring practice 103 that has requested the automated creation of referrals by a service associated with, e.g., referrals platform 104. For example, in step 518, it may be determined if the sender of the message (e.g., a referring practice) has given authorization for the creation of referrals from a CCD. As another example, it may be determined if a manager of a referrals system has given authorization for the creation of referrals from a CCD. If no map exists, then creation of a referral using the CCD may not proceed. However, if no map exists, the CCD may be compared to stored referrals to determine whether it matches any existing referrals. Flow may therefore continue to step 506. If, in step 506, no matching referral is found for the CCD, then, according to step 520, the CCD may be stored (e.g., in referrals database 214).

According to step 506, whether a CCD matches the stored referral may be determined. In some embodiments, medical referrals API 208 and/or referrals engine 212 may perform this step by, e.g., comparing data from the stored referral to elements of the CCD. If no or few discrepancies are found between the referral and the CCD, then the CCD can be found to match the referral.

According to step 508, if a CCD and a stored referral match, then the CCD may be attached to the referral. Attaching the CCD to the referral may provide several advantages; for example, the referral and CCD may then be audited to ensure that the referrals creation process was successful. Also, an entity receiving the referral and attached CCD, such as a specialist 106a, 106b to whom a patient is referred, may benefit from having a full document of healthcare information (the CCD) about the patient who is being referred. In some embodiments, if the CCD was received (e.g., in step 510) as a part of a message containing multiple attachments, one or more other attachments that came with the message may be attached to the referral as well.

If a map does exist, e.g., for a referring practice associated with the CCD or otherwise authorizing continuation of the referral creation process, flow may continue to step 522, and a referral may be created containing mapped parameters from the CCD and/or the message, e.g., as has been previously described in method 400. According to step 524, the CCD may be attached to the created referral. In some embodiments, if the CCD was received (e.g., in step 510) as a part of a message containing multiple attachments, other attachments that came with the message and were extracted from the message (in, e.g., step 512) may be attached to the referral. Flow may then return to step 509.

According to step 509, the referral and attached CCD (and potentially other attachments) may then be stored in, e.g., referrals database 214, and/or exported by, e.g., medical referrals API 208. In some embodiments, a single referral and attached CCD (and any other attachments) may be exported to a referring practice, a specialist 106a, 106b, and/or an one or more insurance providers 108a, 108b, 108c. In further embodiments, referrals created by flow 500 and updated with attached CCDs and other attachments, may be sent to the referring practice (either integrated referring practice 102 or referring practice 103) in one or more electronic packages via secure message.

It will be understood that, although the steps in FIG. 5 are laid out in a particular order and in a particular flow, variations on the depicted order and/or flow are contemplated within the scope of this disclosure. For example, one or more steps in FIG. 5 may be repeated, may not be performed, or may be performed in a different order than is depicted in FIG. 5.

Figure 6:
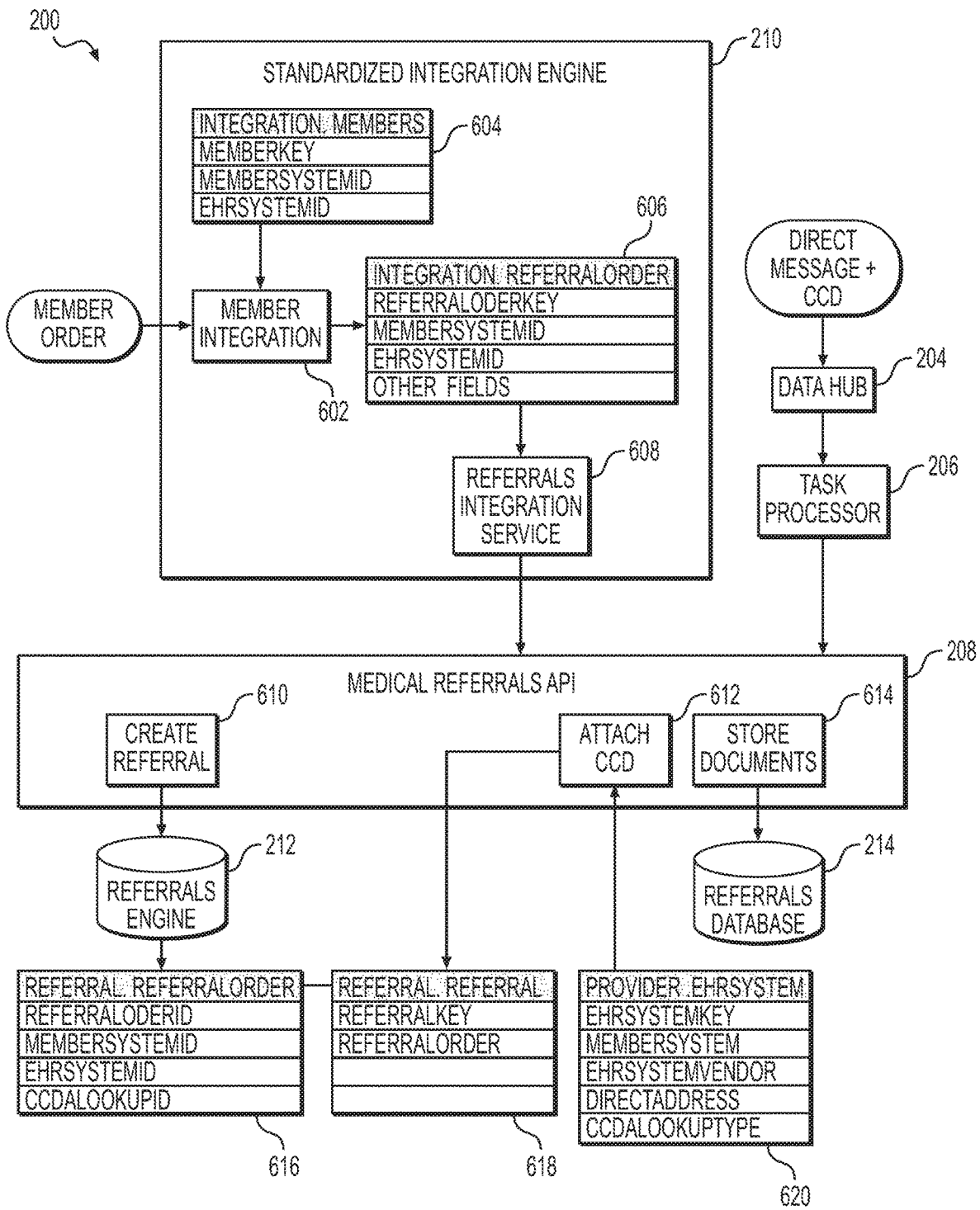
FIG. 6 illustrates another exemplary system and workflow diagram, in accordance with one or more embodiments of the present disclosure.
Figure 7:
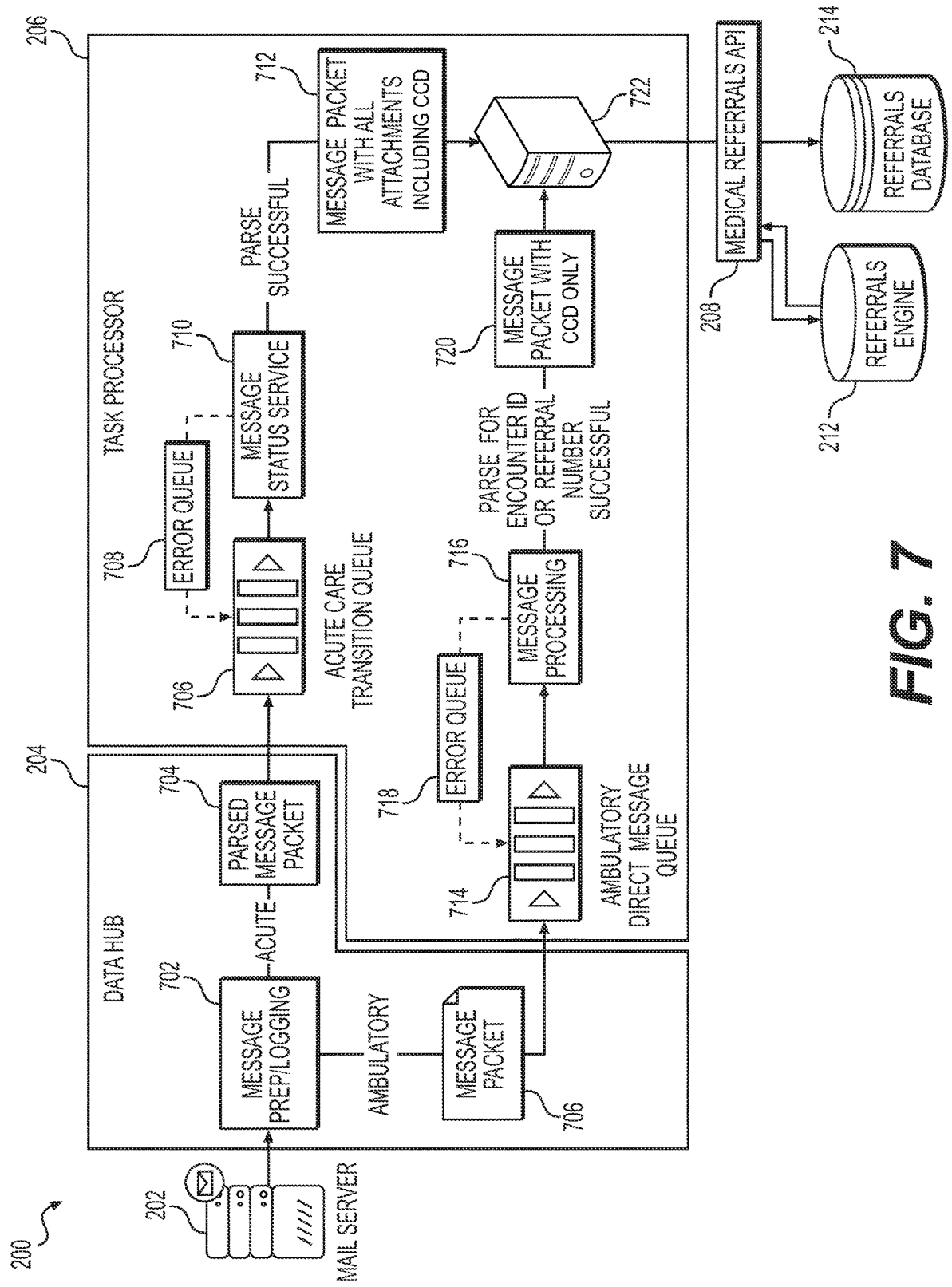
FIG. 7 illustrates a further exemplary system and workflow diagram, in accordance with one or more embodiments of the present disclosure.
Figure 8:
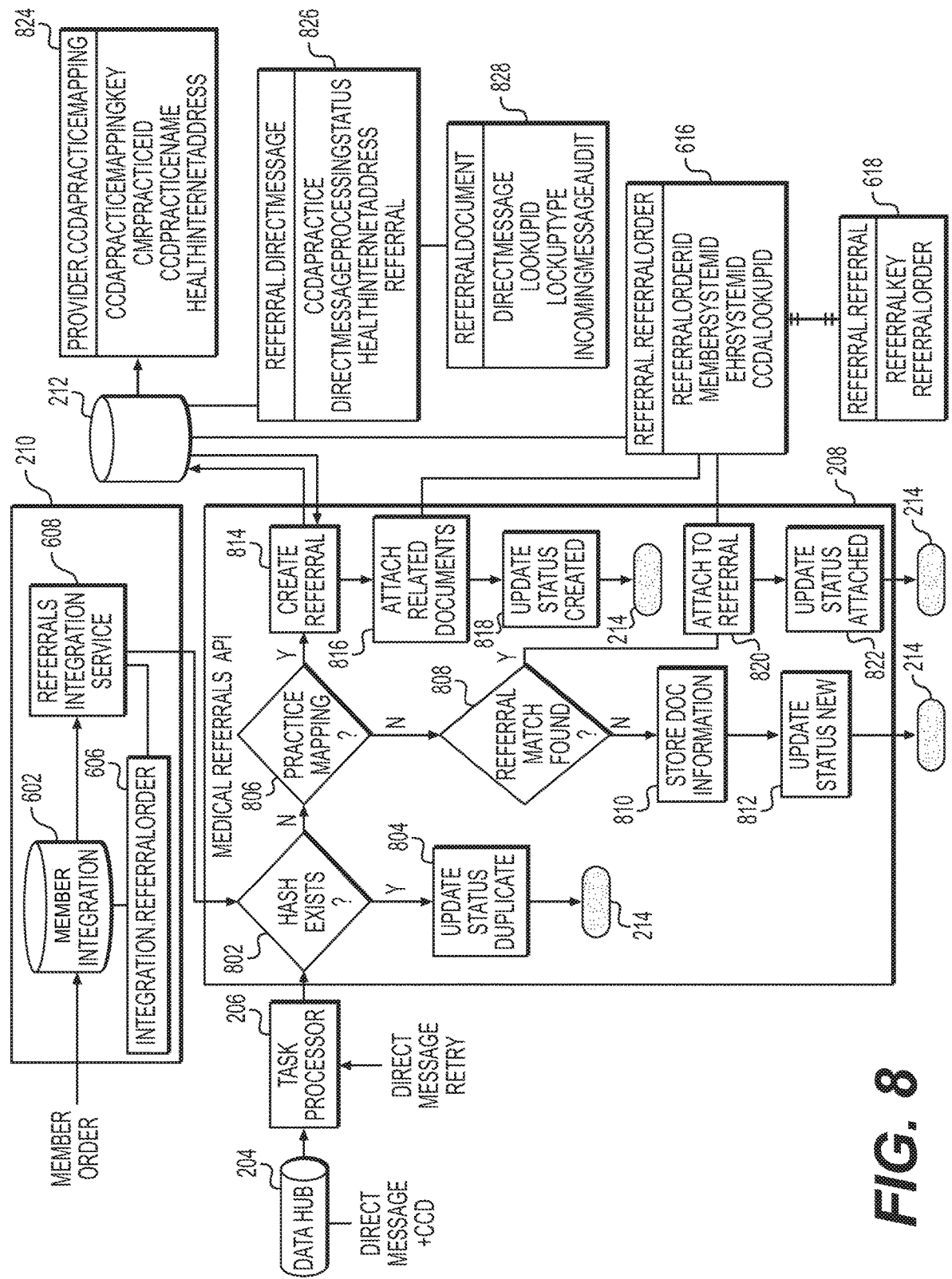
FIG. 8 depicts a further exemplary system and workflow diagram in accordance with one or more embodiments of the present disclosure.

FIGS. 6-8 depict combined system and workflow diagrams which show examples of how the methods and flows described herein may be implemented. It will be understood that these examples are not limiting, and that other modes of implementing the methods and systems herein may be within the purview of one of ordinary skill in the art.

FIG. 6 depicts a partial view of referrals system 200 overlaid with a workflow diagram, including standards-integrated engine 210, medical referrals API 208, data hub 204, task processor 206, referrals engine 212, and referrals database 214. In particular, elements of standards-integrated engine 210, medical referrals API 208, and referrals engine 212 have been expanded. Reference will now be made to particular expanded parts in FIG. 6.

Standards-integrated engine 210 has been expanded to show aspects of an exemplary referrals creation process in further detail. This process corresponds to steps 502, 504, and 505 in FIG. 5. In step 602, upon receiving a referral order at standards-integrated engine 210 (also referred to herein as a "member order"), member integration is verified. For example, standards-integrated engine 210 may determine whether the member order came from an integrated referring member 102 with whose EHR or EMR a referrals service is integrated. Member integration may be verified by, e.g., searching for and finding an identity matching the sender of the member order in a database of integrated members, represented by integrated members module 604. Identity may be verified by, e.g., a member key, a member system ID, and/or an EHR or EMR system ID.

Upon verifying member integration, standards-integrated engine 210 may create or update a referral order module 606 with information about the referral order and the integrated referring member (e.g., integrated referring member 102). This information may include fields necessary to completing the creation of a referral. Flow may then continue through referrals service 608, which may include creation of a referral using information from the integrated referring member's EHR or EMR, as well as from the referral order module 606. The created referral may then be forwarded to medical referrals API 208 for storage of the referral (e.g., step 614) and/or matching and attachment of a CCD to the referral (e.g., step 612, like steps 506, 508). In some embodiments, the created module may additionally or alternatively be returned to the sender of the member order. In some embodiments, the created referral may be forwarded to medical referrals API 208 with one or more modules of identifying data. For example, a system module 620 may include data identifying the member order, the integrated referring practice, the EHR or EMR vendor used by the integrated referring practice, etc. A referral key module 618 may also be associated with a referral, and may be populated with, e.g., a referral key and a referral order identifier.

Medical referral API 208 has also been expanded to show its functions of referral creation 610 (like step 522), attaching of CCDs to referrals (step 612, like step 524), and storing documents and data (e.g., step 614, like step 509). Additionally, several data structures relevant to referral creation and matching are shown. For example, a referral order module 616 may be associated with a created referral, and may be populated with identifying data for a created referral by referrals engine 212. When attempting to match a referral created by, e.g., standards-integrated engine 210 with a CCD received via a message (like step 506), medical referrals API 208 and/or referrals engine 212 may compare modules associated with the created referral and data associated with the CCD.

FIG. 7 depicts another partial view of referrals system 200 overlaid with a workflow diagram, including mail server 202, data hub 204, task processor 206, medical referrals API 208, referrals engine 212, and referrals database 214. Data hub 204 and task processor 206 have been expanded to show workflows contained within each.

In some embodiments, upon receipt of a message containing a CCD from mail server 202, data hub 204 may prepare and log the received message (step 702). Data hub 204 may then sort the received message depending on whether it relates to (e.g., requests or otherwise indicates) a referral of a patient in acute care (e.g., inpatient care) or ambulatory care (e.g., outpatient care). If the message requests or otherwise indicates a referral of a patient in acute care, then data hub 204 may parse the message packet 704 and forward it to an acute care transition queue 706 managed by task processor 206. If the message requests or otherwise indicates a referral of a patient in ambulatory care, then data hub 204 may forward the message packet 706 to an ambulatory message queue 714.

Timing and processing for the acute care transition queue 706 and the ambulatory message queue 714 may differ, due to the number and types of messages in each queue. For example, the acute care transition queue 706 may contain more urgent transfer of care requests than the ambulatory message queue 714. Each queue 706, 714 may be equipped with an error queue 708, 718, respectively. Following the acute care transition queue 706, the message may be parsed to extract all attachments (including, e.g., a CCD and other attachments, such as test results, images, notes, recommendations, etc.) and create a message packet, complete with all attachments in the packet. If the process results in an error, the message may be sent to error queue 708. Similarly, messages in the ambulatory message queue 714 may be parsed for an encounter ID or a referral ID indicating that a referral is desired. Errors in parsing may result in the message being sent to error queue 718. In the case of a message relating to ambulatory care, a message packet with only continuity of care data architecture (e.g., only a CCD) may then be created (step 720). Message packets may be forwarded to data storage 722 and to, e.g., medical referrals API 208.

FIG. 8 depicts another partial view of referrals system 200 overlaid with a workflow diagram, including data hub 204, task processor 206, medical referrals API 208, standards-integrated engine 210, referrals engine 212, and referrals database 214. Also depicted in FIG. 8 are several exemplary data modules 824, 826, 828 (as well as previously described modules 616, 618) which may be used by, e.g., medical referrals API 2008 and referrals engine 212 in the creation and matching of referrals using CCDs. For example, CCD practice mapping module 824 may include or identify information about a CCD being mapped by referrals engine 212, including, e.g., a key authorizing referrals engine 212 to map the CCD, an ID associated with a practice from which the CCD was sent, a name of the practice from which the CCD was sent, and/or information about where the CCD originated and the intended destination of a referral created using the CCD. Direct message module 826 may, for example, include or identify information about a message carrying a CCD, such as, e.g., a practice from which the message originated, a status for whether the message has been processed or not, information about the intended destination of the message, and/or information about a referral created from information in the direct message. A referral identification module 828 may, for example, include or identify information identifying a message from which a referral was created, an ID for the referral, a referral type, and/or whether or not the message from which the referral was created is audited. Additionally in FIG. 8, medical referrals API 208 has been expanded to show an exemplary flow that may be performed as part of the systems and processes disclosed herein.

Upon receipt of a package from task processor 206 at medical referrals API 208, according to step 802, a hash may be created for the received package. The hash may be a combination of all of the documents in the received package in alphabetical order, and thus may be unique to the received package. If the hash is found to exist in stored memory accessible by medical referrals API 208 (e.g., in referrals database 214 or in a separate storage medium particular to medical referrals API 208), then according to step 804, medical referrals API 208 may update a status of the received package in a database (e.g., in referrals database 214) as a duplicate package.

If the package is not a duplicate, then according to step 806, medical referrals API 208 may determine whether a map exists corresponding to an authorization or direction to continue with a referral creation process (like step 518). If no map exists, then according to step 808, medical referrals API 208 may determine whether a referral already exists for a CCD or other document in the received package. If a referral does not exist, the package may be stored according to step 810, and a database, such as referrals database 214, may be updated to include that the package has been stored. For example, an entry may be added to referrals database 214 that reflects the existence of the package in storage, and the entry may include a status indicator, which may be updated to "new" in, e.g., referrals database 214, according to step 812. The "new" status may indicate to medical referrals API 208 that the package has not yet been matched with a referral, and the system may try to match the package to a referral again later. If a referral match is found in step 808, then according to step 820 the package or a part thereof (such as a CCD) may be attached to the existing referral, and a status of the package and/or the referral may be updated to "attached" in, e.g., referrals database 214.

If, in step 806, a map does exist for a practice associated with the received package, then according to step 814, medical referrals API 208 may instruct referrals engine 212 to create a referral using, e.g., a CCD in the package. Upon creation of a referral, medical referrals API 208 may attach any remaining documents, as well as the CCD, to the referral (step 816). A status of the package and the referral may be updated to "created" in, e.g., referrals database 214 (step 818). Upon a referral being created or a CCD or package being attached to an existing referral, the referral, package, and/or CCD may be stored and/or exported as has been described elsewhere herein.

FIGS. 9-13 illustrate, in schematic form, exemplary data structures that may be created or updated by the systems disclosed herein, and/or as a part of the methods disclosed herein. Data structures such as those illustrated in FIGS. 9-13 may be software data structures encoded in, e.g., one or more servers, processors, databases, and/or engines, either in a single physical location or in multiple locations (e.g., a remote server or the cloud). In some embodiments, data structures such as those illustrated in FIGS. 9-13 may serve, for example, as frameworks for storing or manipulating information that is created, modified, sent, and/or received in various parts of, e.g., referrals system 200. In some embodiments, data structures such as those illustrated in FIGS. 9-13 may serve as frameworks for parsing information in, e.g., medical referrals API 208, storing information in, e.g., referrals database 214, and/or manipulating information in, e.g., referrals engine 212. In further embodiments, these data structures may be used by the computers of integrated referring practice 102, referring practice 103, specialists 106a, 106b, and/or insurance providers 108a, 108b, 108c.

In some embodiments, data structures such as those illustrated in FIGS. 9-13 may be divided into modules as further described below, and may contain the data listed in each illustrated module, or may contain information identifying, listing, pointing to, or otherwise pertaining to the types of data, listed in each illustrated module. In some embodiments, the modules may be linked to one another as illustrated in each of the figures, allowing for a computer, application, system, or user accessing a module to also access data in a linked module. Moreover, in some embodiments, the modules may each have a key, which may be a code, string, or other digital access method with which a computer, application, system, or user may access the information or data in the module corresponding to the key.

In some embodiments, data structures such as those illustrated in FIGS. 9-13 may be used as a part of an auditing process. An auditing process may include, for example, reviewing and verifying what messages, CCDs, referrals, transfer of care documents, and other data has been sent or received, as well as the status of such documents, files, and data. In further embodiments, data structures such as those illustrated in FIGS. 9-13 may be used by retry processes. A retry process may, for example, access a data structure for a CCD for which referral creation was unsuccessful, in order to retrieve data associated with the CCD and attempt referral creation again.

It will be understood that the data structures disclosed in FIGS. 9-13 are exemplary, and are not intended to be limiting with regard to the systems and methods disclosed herein. Multiple variations and elaborations on the data structures disclosed in FIGS. 9-13 will be considered well within the capabilities of one of ordinary skill in the art.

Figure 9:
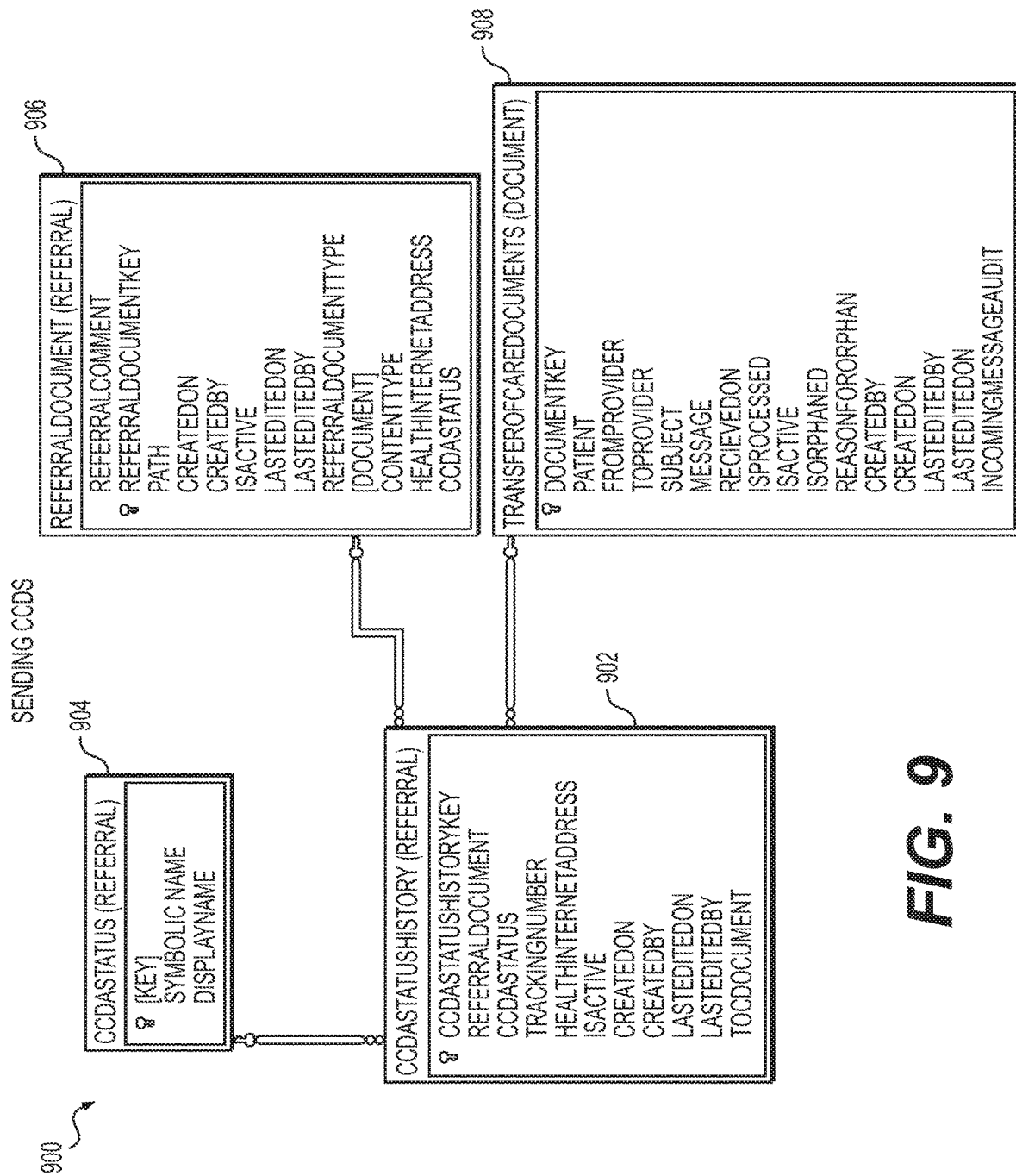
FIG. 9 depicts an exemplary map of data for sending CCDs, in accordance with one or more embodiments of the present disclosure.

FIG. 9 illustrates, in schematic form, an exemplary CCD data structure 900 including an organizational framework for information pertaining to a CCD that is to be sent, or that has been sent, with a message. CCD data structure 900 may include a status history module 902, which may contain an organization of information relating to the CCD's status, such as, e.g., identity of a referral document associated with a CCD, status of the CCD (e.g., whether it has been sent, whether it is being processed, whether it was successfully sent, or whether sending the CCD resulted in a failure), a tracking number, a health internet address which may provide information regarding the sender and/or intended recipient of the CCD or a document associated with the CCD, an indication of whether the CCD is active, a date on which the CCD was created, the identity of a person or entity who created the CCD, when the CCD was last edited, who last edited the CCD, and/or a table of contents for the CCD. Status history module 902 may be linked to, e.g., a CCD status module 904, which may contain, e.g., information regarding a symbolic name and/or a display name for the CCD.

Status history module 902 may also be linked to, e.g., a referral document module 906, which may contain information regarding a referral that has been or will be created using the information in the CCD. For example, referral document module 906 may contain information regarding comments on a referral, a path or physical location of the referral, when the referral was created and by whom or what, whether the referral is active, when and by whom the referral was last edited, a document type associated with the referral, the referral document itself, a type of content within the referral document, a health internet address which may provide information regarding the sender and/or intended recipient of the referral, and/or the information contained in CCD status module 904.

Status history module 902 may also be linked to, e.g., a transfer of care document module 908, which may contain information regarding a transfer of care document that has been or will be created using the information in the CCD. For example, transfer of care document module 908 may include information regarding, e.g., the patient being transferred, the practice or healthcare provider transferring the patient, the practice or healthcare provider receiving the transferred patient, any messages sent with the document, when the transfer of care document was received, whether the transfer was processed, whether the transfer is active, whether the patient is orphaned (e.g., no longer associated with the transferring practice or healthcare provider), any reason why the patient is orphaned, when and by whom the transfer of care document was created, when and by whom the transfer of care document was last edited, and/or the identity, location, and/or result of any audit of the transfer of care and/or messages associated with the transfer of care.

Figure 10:
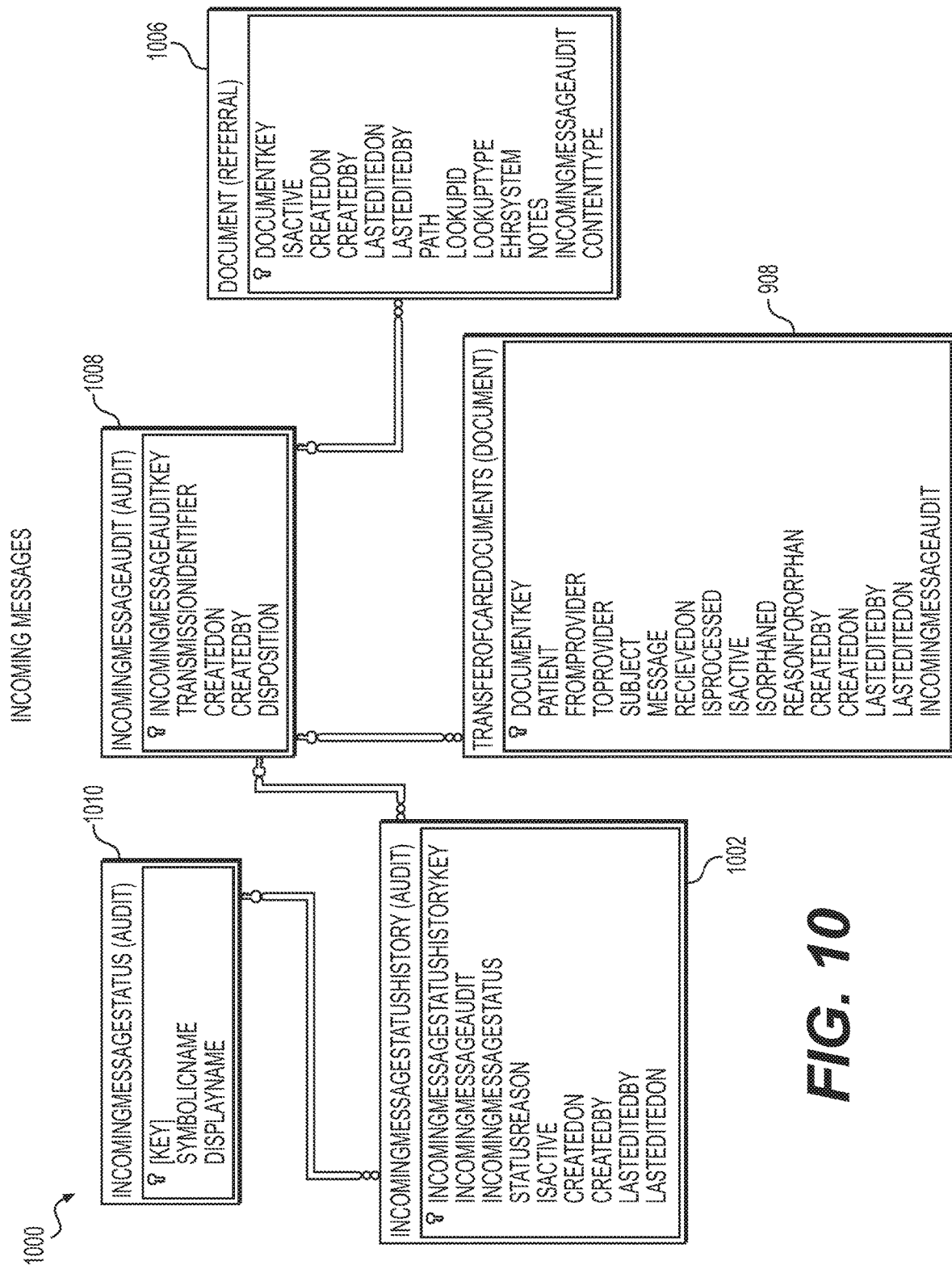
FIG. 10 depicts an exemplary map of data for incoming messages, in accordance with one or more embodiments of the present disclosure.

FIG. 10 illustrates, in schematic form, an exemplary message data structure 1000 including an organizational framework for information pertaining to a message, such as an incoming message attached to a transfer of care document, or a message to which a referral document is attached. Message data structure 1000 may include, for example, transfer of care document module 908 or a copy thereof, thus potentially creating an overlap or a link with CCD data structure 900. Message data structure 1000 may further include a message status history module 1002 containing information pertaining to the status history of a message. A message status module 1010 may be linked to the message status history module 1002, the message status module 1010 containing information pertaining to a symbolic name or a display name for the message. The message data structure 1000 may also contain a referral module 1006, containing information similar in scope to referral document module 906. Referral module 1006 may include information regarding identification of the referral, such as a referral ID, a referral type, an identifier of the EHR or EMR of a practice requesting a referral, and/or a status of an audit of the message. As is illustrated by referral document module 906 and referral module 1006, variations on the data structures and modules disclosed herein are contemplated by this disclosure. Message data structure 1000 may also contain a message audit module 1008, which may include information with regard to when and how a message was audited, and the disposition of the audit. In some embodiments, transfer of care document module 908 may contain information identifying the location and/or contents of message audit module 1008, thus creating a link between CCD data structure 900 and message data structure 1000.

Figure 11:
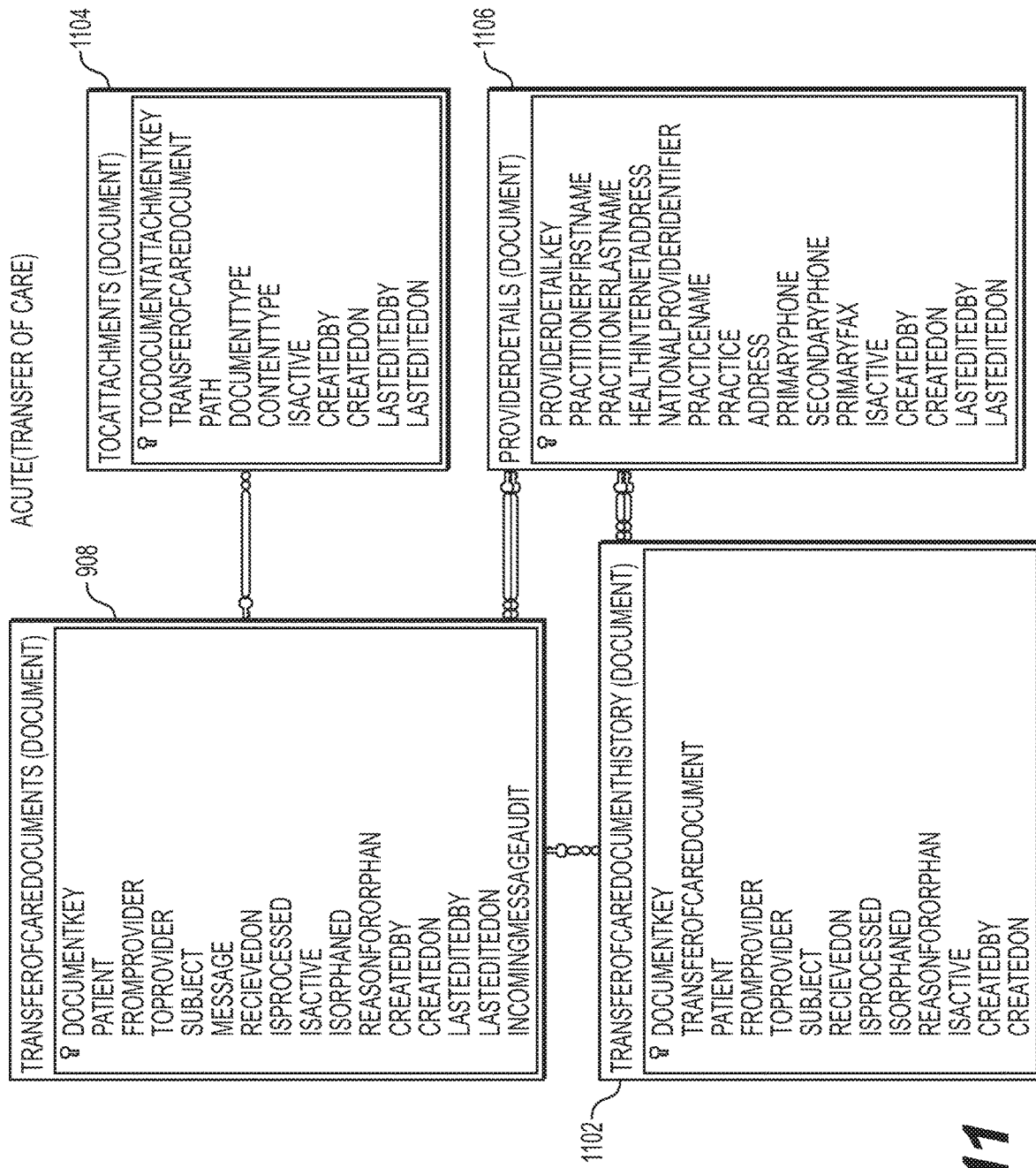
FIG. 11 depicts an exemplary map of data for an acute referral.

FIG. 11 illustrates, in schematic form, an exemplary transfer of care data structure 1100, including an organizational framework for information pertaining to a transfer of care document. In some embodiments, transfer of care data structure 1100 may be associated with acute transfers of care, such as inpatient transfers of care in a hospital. Transfer of care data structure 1100 may include, for example, transfer of care document module 908, thus creating an overlap or link with CCD data structure 900. A transfer of care attachments module 1104 may be linked to transfer of care document module 908, and may include information pertaining to, for example, any attachments intended to be sent or stored with a transfer of care document, such as a document type for an attachment, a content type for the attachment, and/or an identifier of the transfer of care document to which the attachment may be attached. Attachments may include, for example, images, laboratory results, test results, and the like. Transfer of care data structure 1100 may also include, for example, a transfer of care document history module 1102, containing information pertaining to the history of a created or stored transfer of care document, such as, for example, a patient associated with the transfer of care document. Additionally, a provider details module 1106 may be linked to the transfer of care document module 908 and the transfer of care document history module 1102, and may include information pertaining to the practice that created or requested the creation of the transfer of care document. For example, provider details module 1106 may include information pertaining to the name, address, and/or other contact information of the practice, and/or identifying information of a particular individual, such as a doctor or other healthcare practitioner who is a member of the practice.

Figure 12:
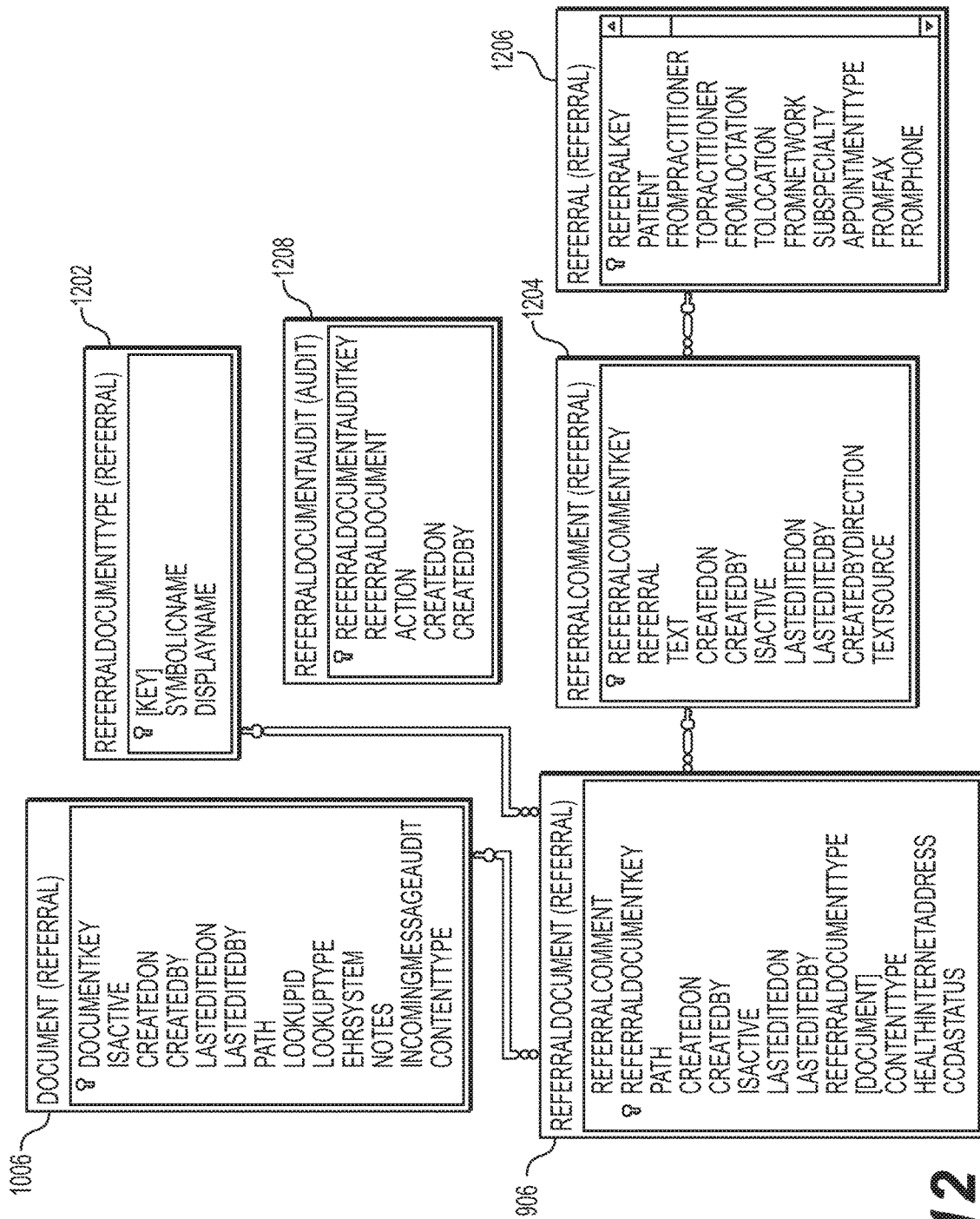
FIG. 12 depicts an exemplary map of data for an ambulatory referral.

FIG. 12 illustrates, in schematic form, an exemplary referral data structure 1200, including an organizational framework for information pertaining to a referral document. In some embodiments, referral data structure 1200 may be used for ambulatory, or outpatient, referrals. Referral data structure 1200 may include, for example, referral module 1006 and referral document module 906, thus potentially creating a link or overlap with message data structure 1000 and a link or overlap with CCD data structure 900. A referral document type module 1202 may be linked to the referral document module 906, and may include information pertaining to an identity of a referral document, such as, for example, a display or symbolic name for the referral document. A referral comment module 1204 may include information pertaining to a comment created on a referral, such as, for example, the text of a comment, when and by whom the comment was created, and/or when and by whom the comment was last edited. A referral module 1206 may contain an organization of information within the referral itself, such as, for example, the identity of a practice from whom the referral is to be issued, the identity of a practice to whom a patient is being referred, the network of the referring practice, a specialty of the practice to whom the patient is being referred, an appointment type, contact information for the referring practice and the practice to whom the patient is being referred, etc. A referral document audit module 1208 may include information pertaining to whether and how a referral or referral document was audited, such as when an audit was begun and by whom, and what action is to be taken on an audited referral.

Figure 13:
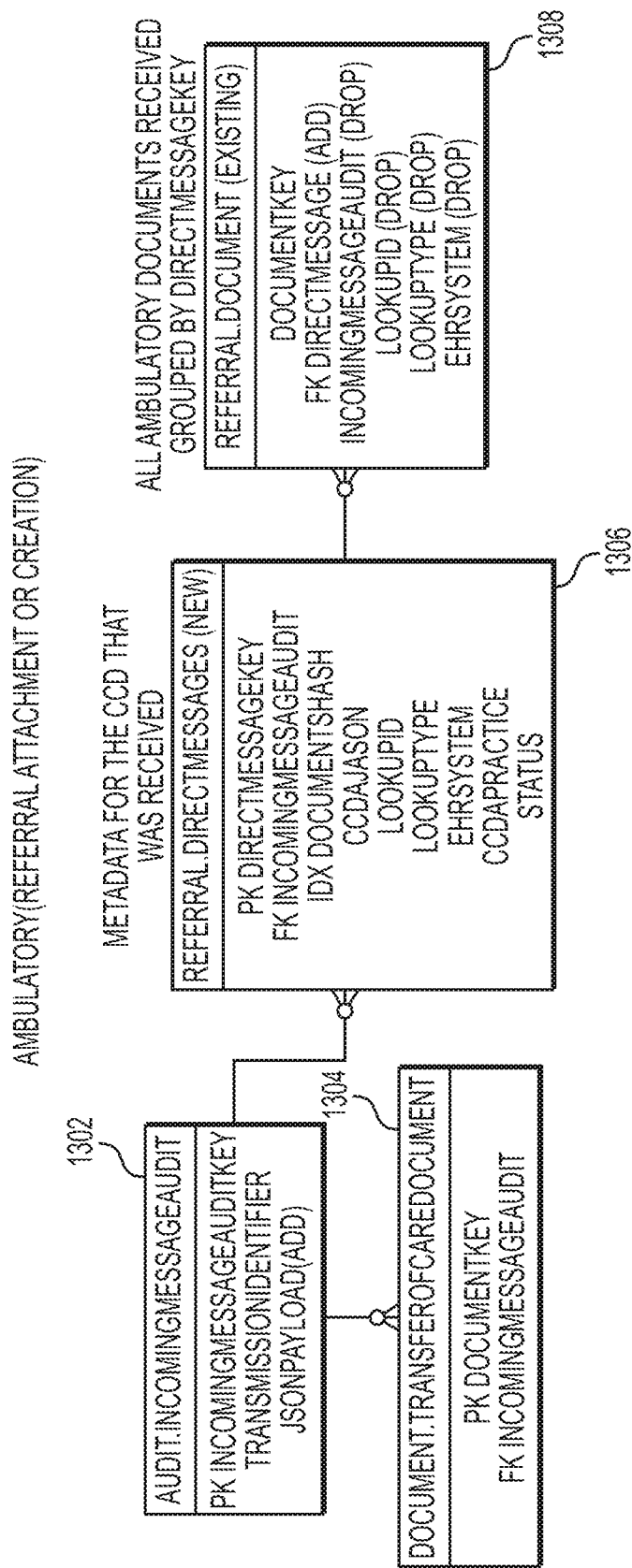
FIG. 13 depicts another exemplary map of data for an ambulatory referral.

FIG. 13 illustrates, in schematic form, another exemplary referral data structure 1300. Referral data structure 1300 may include, for example, an incoming message audit module 1302, which may contain information pertaining to whether an incoming message containing a CCD has been audited. Referral data structure 1300 may also include a transfer of care document module 1304 identifying a transfer of care document associated with an audit. Referral data structure 1300 may also include a CCD metadata module 1306 which may contain metadata for a CCD received with the incoming message, such as, for example, a hash created for the CCD, an ID for the CCD, an identification of an EHR or EMR from which the CCD was made, and/or a CCD status, etc. Referral data structure 1300 may also include an existing ambulatory referral document module 1308, which may contain information pertaining to an existing referral associated with a received CCD, such as an ID and/or a type of the referral, etc.

Figure 14:
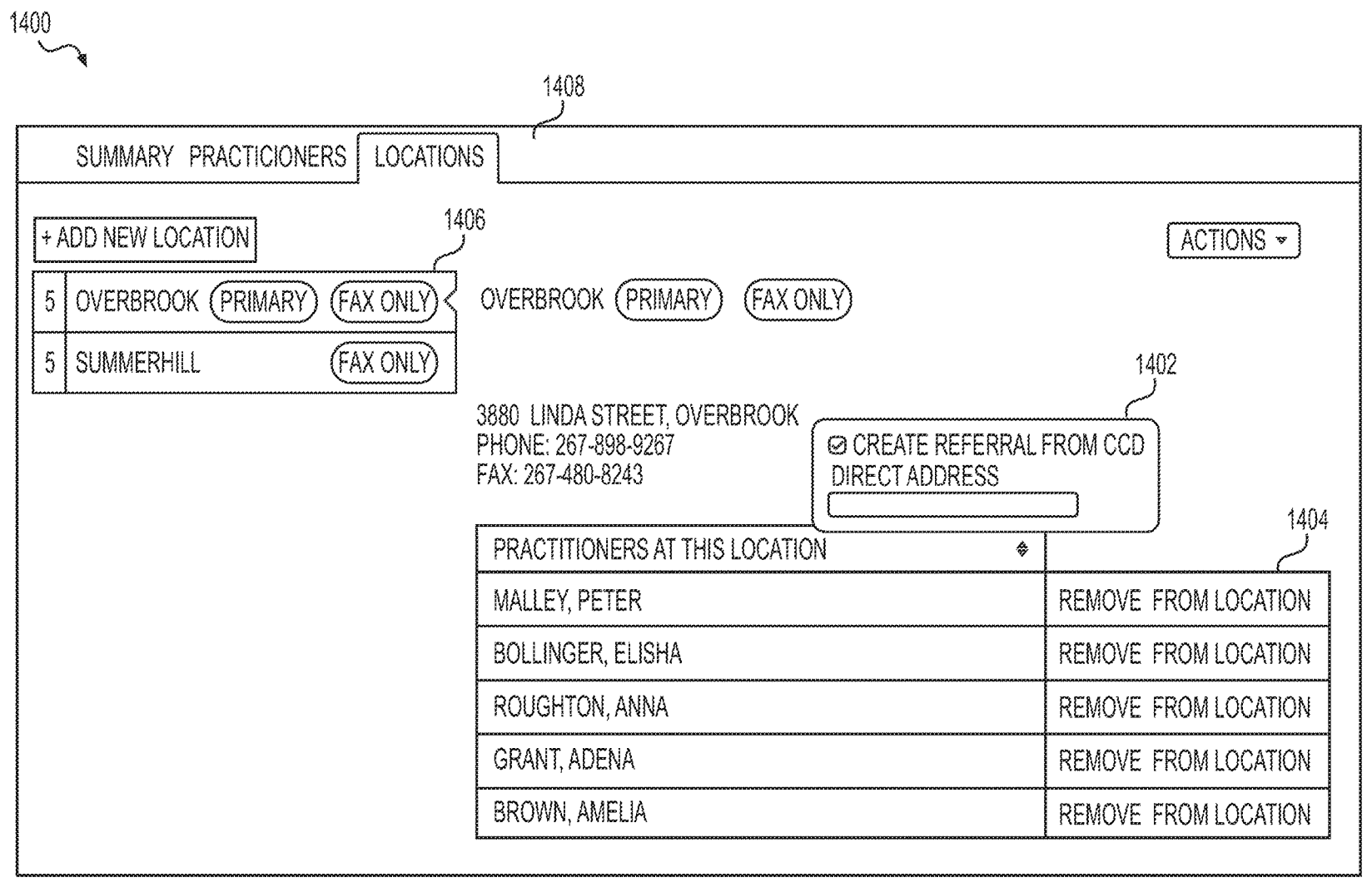

The systems and methods disclosed herein may also include tools for user interaction. For example, FIG. 14 depicts an exemplary graphical user interface that may be generated by, e.g., referrals platform 104 for display to a device associated with, e.g., integrated referring practice 102, referring practice 103, referrals platform 104, specialists 106a, 106b, or insurance providers 108a, 108b, 108c. The user interface depicted in FIG. 14 includes, for example, information about a given practice. A menu bar 1408 may provide options to view summary information about a practice, practitioners associated with the practice, and geographical locations of the practice. The location tab, which is depicted in FIG. 14, may include, for example, a selectable option 1402 to create a referral from a CCD. The location tab may further include a list of practitioners 1404 at given location, as well as a summary of viewable locations 1406.

In one exemplary embodiment, a user interface such as that depicted in FIG. 14 may be displayed on a device of, e.g., an integrated referring practice 102 or referring practice 103. Upon selection of option 1402 to create a referral from a CCD, the device may instruct a computer (e.g., a computer of the integrated referring practice 102 or referring practice 103, or a standards-integrated engine 210 or part thereof) to create or retrieve a CCD generated using the EHR or EMR of the integrated referring practice 102 or referring practice 103. The device may then pair the CCD with a message and send the message and CCD to referrals platform 104 over, e.g., network 110. The message and CCD may then be parsed as has been described herein.

One of ordinary skill in the art will understand that the particulars of the user interface depicted in FIG. 14 are exemplary, and that variations upon the depicted user interface may be made in order to customize the user interface to a particular user and/or set of queries. For example, an additional tab (not shown) may list recently-completed referrals made from a given practice. As a further example, user authentication elements may be added to the user interface in order to secure access to confidential patient data.

Thus, exemplary embodiments of the present disclosure provide systems and methods for creating, sending, and/or receiving messages containing patient summary information, digitally parsing information from messages containing patient summary information, and generating electronic files and/or documents using the parsed information. Advantageously, aspects of the present disclosure, when implemented, may allow for the automation of tasks not previously capable of being done by a computer, without a practitioner integrating its EHR or EMR system with a standardized system. For example, receiving an electronic file, such as a CCD, via a message, such as a Direct message, parsing patient data from the electronic file, and generating a referral using the parsed patient data may allow for computer creation of a referral without having to establish, e.g., a dedicated connection between an EHR or EMR of a health practice and a referrals service. In this manner, generating referrals and other electronic health-related documents according to embodiments disclosed and claimed herein may be accomplished using significantly less processing power, hardware, software, and/or resources. In particular, resources used by, e.g., a referring practice 103 and/or a referring member practice 102 may be decreased, thus allowing referring practices having limited resources to request automated referrals without submitting to a lengthy and resource-consuming integration process.

Aspects of the present disclosure may be embodied as a system, method, or computer program product. Embodiments of the present disclosure may be implemented using hardware, software, or a combination of both hardware and software. For example, aspects of the present disclosure may take the form of an entirely hardware embodiment, an entirely software embodiment (including firmware, resident software, micro-code, etc.) or an embodiment combining software and hardware, sometimes referred to herein as a "system." Furthermore, aspects of the present disclosure may take the form of one or more computer program product(s) embodied in one or more computer readable medium(s) having computer readable program code embodied thereon.

The systems disclosed herein may include software, information processing hardware, and various processing steps, as described herein. The features and steps of the various embodiments may be implemented in machine or computer executable instructions. The instructions may be used to cause a processor, which may be programmed with the instructions, to perform the steps of the various embodiments. Alternatively, the steps of the various embodiments may be performed by specific hardware components that contain hard-wired logic for performing the steps, or by any combination of programmed computer components and custom hardware components.

The terminology used herein is for the purpose of describing particular embodiments only and is not intended to be limiting of the disclosure. As used herein, the singular forms "a," "an" and "the" are intended to include the plural forms as well, unless the context clearly indicates otherwise. It will be further understood that the terms "comprises" and/or "comprising" and "includes" and/or "including," when used in this specification, specify the presence of stated features, integers, steps, operations, elements, and/or components, but do not preclude the presence or addition of one more other features, integers, steps, operations, element components, and/or groups thereof.

Although some embodiments of the invention have been described herein, it will be understood that the invention is not limited to the specific embodiments disclosed herein but is capable of numerous modifications by one of ordinary skill in the art. The present disclosure has been presented for purposes of illustration and description, but is not intended to be exhaustive or limited to the disclosure in the form or forms disclosed. It will be understood that the materials used and technological details may be slightly different or modified from the descriptions herein without departing from the methods and compositions disclosed and taught by the present invention. Many variations and modifications will be apparent to those of ordinary skill in the art. Any corresponding structures, materials, steps, acts, and equivalents of all means or step plus function elements in the claims below are intended to include any structure, material, or act for performing the function in combination with other claimed elements as specifically claimed.

The invention claimed is:

1. A system for generating an electronic referral document, the system comprising one or more computing devices, and the system configured to at least:
   receive a plurality of electronic files comprising first information of a patient, wherein (a) the first information is in a standardized format, and (b) the plurality of electronic files were received via a secure message;
   generate an electronic referral document associated with an entity, wherein generating the electronic referral document comprises:
   in an instance in which the entity has received authorization for referral generation:
   parse the first information to extract second information of the patient,
   map the second information to a template for an electronic referral document for the patient, and
   generate the electronic referral document comprising the second information based at least in part on the mapping; and in an instance in which the entity has not received authorization for referral generation:
determine whether the plurality of electronic files correspond to a previously-generated electronic referral document by:
generating a hash corresponding to the plurality of electronic files, and
determining whether the hash matches one or more previously generated hashes, and
responsive to determining that the hash matches at least one of the one or more previously generated hashes, attaching at least one of the plurality of electronic files to the previously-generated electronic referral document to generate a referral package.

2. The system of claim 1, wherein at least one of the plurality of electronic files comprises is a continuity of care document (CCD).

3. The system of claim 1, wherein the electronic referral document comprises a referral for at least one of acute care, ambulatory care, post-acute care, imaging procedures, laboratory procedures, or other diagnostic or therapeutic procedure.

4. The system of claim 1, wherein the standardized format is in an extensible markup language (XML) architecture.

5. The system of claim 1, wherein the electronic referral document is provided to a computing device of at least one of a healthcare practice, a specialist, a patient, or an insurance provider.

6. The system of claim 1, wherein the system is further configured to extract the plurality of electronic files from the secure message.

7. A computer program product for generating an electronic referral document, the computer program product comprising executable code for execution by one or more computing devices, the executable code configured to at least:
receive a plurality of electronic files comprising first information of a patient, wherein (a) the first information is in a standardized format, and (b) the plurality of electronic files were received via a secure message;
generate an electronic referral document associated with an entity, wherein generating the electronic referral document comprises:

in an instance in which the entity has received authorization for referral generation:
parse the first information to extract second information of the patient,
map the second information to a template for an electronic referral document for the patient, and
generate the electronic referral document comprising the second information based at least in part on the mapping; and
in an instance in which the entity has not received authorization for referral generation:
determine whether the plurality of electronic files correspond to a previously-generated electronic referral document by:
generating a hash corresponding to the plurality of electronic files, and
determining whether the hash matches one or more previously generated hashes, and
responsive to determining that the hash matches at least one of the one or more previously generated hashes, attaching at least one of the plurality of electronic files to the previously-generated electronic referral document to generate a referral package.

8. The computer program product of claim 7, wherein at least one of the plurality of electronic files comprises is a continuity of care document (CCD).

9. The computer program product of claim 7, wherein the electronic referral document comprises a referral for at least one of acute care, ambulatory care, post-acute care, imaging procedures, laboratory procedures, or other diagnostic or therapeutic procedure.

10. The computer program product of claim 7, wherein the standardized format is in an extensible markup language (XML) architecture.

11. The computer program product of claim 7, wherein the electronic referral document is provided to a computing device of at least one of a healthcare practice, a specialist, a patient, or an insurance provider.

12. The computer program product of claim 7, wherein the executable code is further configured to extract the plurality of electronic files from the secure message.

* * * * *